US 6,714,814 B2

(12) United States Patent
Yamada et al.

(10) Patent No.: US 6,714,814 B2
(45) Date of Patent: Mar. 30, 2004

(54) BIOELECTRICAL IMPEDANCE MEASURING APPARATUS

(75) Inventors: Yasushi Yamada, Tokyo (JP); Yoshinori Fukuda, Akita (JP); Katsumi Takehara, Tokyo (JP); Maki Ishigooka, Omagari (JP); Tsutomu Miyoshi, Asaka (JP)

(73) Assignee: Tanita Corporation, Tokyo (JP)

( * ) Notice: Subject to any disclaimer, the term of this patent is extended or adjusted under 35 U.S.C. 154(b) by 420 days.

(21) Appl. No.: 09/810,172

(22) Filed: Mar. 19, 2001

(65) Prior Publication Data
US 2001/0030546 A1 Oct. 18, 2001

(30) Foreign Application Priority Data

| Mar. 30, 2000 | (JP) | 2000-093830 |
|---|---|---|
| Mar. 30, 2000 | (JP) | 2000-093831 |
| Mar. 30, 2000 | (JP) | 2000-093832 |
| Apr. 27, 2000 | (JP) | 2000-128049 |
| Jun. 28, 2000 | (JP) | 2000-194245 |

(51) Int. Cl.$^7$ ................................ A61B 5/05
(52) U.S. Cl. .............. 600/547; 600/548; 600/384; 600/393
(58) Field of Search ................. 600/547, 548, 600/372, 382, 384, 393, 383, 386; 324/691, 692

(56) References Cited

U.S. PATENT DOCUMENTS

| 5,642,734 A | | 7/1997 | Ruben et al. | |
|---|---|---|---|---|
| 6,408,204 B1 | * | 6/2002 | Hirschman | 600/547 |
| 6,459,931 B1 | * | 10/2002 | Hirschman | 600/547 |
| 6,516,222 B2 | * | 2/2003 | Fukuda | 600/547 |
| 6,519,491 B2 | * | 2/2003 | Ishikawa et al. | 600/547 |
| 6,526,315 B1 | * | 2/2003 | Inagawa et al. | 600/547 |
| 6,532,385 B2 | * | 3/2003 | Serizawa et al. | 600/547 |
| 6,552,553 B2 | * | 4/2003 | Shoji et al. | 324/692 |

FOREIGN PATENT DOCUMENTS

| EP | 0 926 488 | 6/1999 |
|---|---|---|
| JP | 10-014899 | 1/1998 |
| JP | 10 174679 | 6/1998 |
| JP | 11-070093 | 3/1999 |
| WO | WO 99/09883 | 3/1999 |

* cited by examiner

Primary Examiner—Henry Bennett
Assistant Examiner—Fadi H. Dahbour
(74) Attorney, Agent, or Firm—McDermott, Will & Emery

(57) ABSTRACT

Disclosed is a impedance measuring apparatus which is easy to use, and which is guaranteed to be free of incorrect measurement caused by some joints appearing in the current flowing passage intervening between two selected body parts and by the indefinite length between two selected body parts. The measuring apparatus of the present invention limits the place of the body under measurement to "one body region", i.e. a selected joint-to-joint body portion or joint-free body portion such as the forearm extending from the wrist to the elbow or the portion extending from the ankle to the knee, and comprises a housing having a contact surface to be applied to one selected body region; a first pair of measurement current supplying electrodes so placed on the contact surface that the one selected body region may be put in contact with the current electrodes; and a first pair of voltage measuring electrodes so placed on the contact surface between the pair of current electrodes that the one selected body region may be put in contact with the voltage electrodes.

27 Claims, 16 Drawing Sheets

BIOELECTRICAL IMPEDANCE MEASURING APPARATUS

BACKGROUND OF THE INVENTION

1. Field of the Invention

The present invention relates to a bioelectrical impedance measuring apparatus which measures the bioelectrical impedance of a living body, and relates to a bioelectrical impedance measuring apparatus which measures body fat, body water, pulse, blood pressure and such like as well as a bioelectrical impedance of a living body.

2. Prior Art

Some examples of conventional bioelectrical impedance measuring apparatus include a cable-connected electrode type of impedance meter 10, a hand-held electrode type of impedance meter 20, and a foot sole-contacting electrode type of impedance meter 30. As shown in FIG. 1, the cable-connected electrode type of impedance meter 10 has a pair of measurement current supplying electrodes 12a, 12b and a pair of voltage measuring electrodes 13a, 13b connected to its cables 11 (hereinafter, a measurement current supplying electrode is called a "current electrode" and a voltage measuring electrode is called a "voltage electrode" in the specification and claims). In measuring bioelectrical impedance, these electrodes are attached on both hands, both feet or one hand and one foot to measure the bioelectrical impedance appearing therebetween. As shown in FIG. 2, the hand-held electrode type of impedance meter 20 has a pair of current electrodes 22a, 22b and a pair of voltage electrodes 23a, 23b placed on its opposite grips 21a, 21b. In measuring bioelectrical impedance, these electrodes are gripped in both hands to measure the bioelectrical impedance appearing therebetween. As shown in FIG. 3, the foot sole-contacting electrode type of impedance meter 30 has a pair of current electrodes 32a, 32b and a pair of voltage electrodes 33a, 33b placed on its platform 31. A user who wants to measure his bioelectrical impedance stands on the platform, thus measuring the bioelectrical impedance appearing between his feet. Thus, all of these apparatuses require that the bioelectrical impedance be measured by applying two pairs of electrodes to two selected body parts, such as both hands, both feet, or one hand and one foot.

These conventional bioelectrical impedance measuring apparatuses measure bioelectrical impedance by applying two pairs of electrodes to two selected body parts, such as both hands, both feet, or one hand and one foot, and therefore, there must be joints appearing in the current-flowing passage from one body part (or one electrode) to the other body part (or the other electrode), which was found by the inventor to be one major cause for incorrect measurement; during measurement the body sections may be bent or twisted at their joints, thus the object under measurement remains not stationary.

The total distance (for example, two arm lengths plus the trunk width) from one selected body part (one hand) to the other (the other hand) varies significantly with individuals, and therefore, accurate measurements can be hardly expected.

The handling of elongated cables and applying electrodes to selected body parts is inconvenient to use.

One object of the present invention is to provide an improved bioelectrical impedance measuring apparatus which is easy to use, and which is guaranteed to be free of incorrect measurement caused by some joints appearing in the current flowing passage intervening between two selected body parts and by the indefinite length between two selected body parts.

SUMMARY OF THE INVENTION

To attain this object the place of the body under measurement is limited to a selected joint-to-joint body portion (or joint-free body portion) such as the forearm extending from the wrist to the elbow or the portion extending from the ankle to the knee. Such a selected joint-to-joint body portion is called "one body region" in the specification and claims.

Specifically a bioelectrical impedance measuring apparatus according to a first aspect of the present invention comprises a housing having a contact surface to be applied to one selected body region, the housing having an alternating current supplying device, a voltage measuring device and an arithmetic unit equipped therewith; a first pair of current electrodes so placed on the contact surface that the one selected body region may be put in contact with the current electrodes; and a first pair of voltage electrodes so placed on the contact surface between the pair of current electrodes that the one selected body region may be put in contact with the voltage electrodes; the alternating current supplying device supplying the first pair of current electrodes with alternating current; the voltage measuring device measuring the voltage appearing between the pair of voltage electrodes; and the arithmetic unit calculating the bioelectrical impedance from the supplying alternating current and the measured voltage.

The housing may include a rest whose upper surface defines the contact surface to be applied to the one selected body region, the contact surface being like a semi-cylindrical trough, and the current and voltage electrodes being so curved that they may be almost coplanar with the semi-cylindrical contact surface.

The bioelectrical impedance measuring apparatus may further comprises a cover member capable of pushing the one selected body region against the two pairs of electrodes.

A second pair of current electrodes and a second pair of voltage electrodes may be placed on the surface of the cover member which surface confronts the contact surface of the rest, the second electrodes being arranged in the same order and at same intervals as the counter first electrodes, thus sandwiching the one selected body region therebetween; and the alternating current supplying device may supply one and same alternating current to the first and second pairs of current electrodes simultaneously, making the two sets of confronting current electrodes function as a single composite pair of current electrodes; and the voltage measuring device may measure the voltage appearing between the first and second pairs of voltage electrodes, making the two sets of confronting voltage electrodes function as a single composite pair of voltage electrodes.

The bioelectrical impedance measuring apparatus may further comprise a positioning member which permits the one selected body region to be put in correct position, the positioning member being capable of effecting so positional adjustment as to fit on the one selected body region.

The one selected body region may be the right or left forearm, and the positioning member is a hand grip and/or an elbow rest.

The housing may include a rest whose upper surface defines the contact surface to be applied to the one selected body region, and a cover member pivotally fixed to one longitudinal edge of the rest, thereby permitting the one selected body region to be sandwiched between the rest and the cover member which is put in its closed position; and the first pairs of current and voltage electrodes may be placed on the surface of the cover member instead of the contact surface to push the two pairs of electrodes against the one selected body region lying on the contact surface of the rest.

The bioelectrical impedance measuring apparatus may further comprise a positioning member which permits the one selected body region to be put in correct position, the positioning member being capable of effecting so positional adjustment as to fit on the one selected body region.

The one selected body region may be the right or left forearm, and the positioning member is a hand grip and/or an elbow rest.

The one selected body region may be the right or left forearm.

The one selected body region may be the part of the right or left leg below the knee and above the ankle.

The bioelectrical impedance measuring apparatus may further comprise a display placed on a selected place of the housing other than the contact surface.

The housing may be so shaped and sized that a user can hold it in one hand while applying the contact surface to the one selected body region, still permitting the display to remain in sight.

The housing may have indentations formed on its opposite sides, on which indentations the fingers are placed, thereby facilitating the holding of the housing in one hand.

The display may be so arranged that the vertical direction of the display is orthogonally traverse to the direction in which the first pairs of current and voltage electrodes are aligned side by side, thereby facilitating the seeing of the information appearing in its screen.

The housing may have a display placed at a selected place other than the contact surface and a grip portion; and a recess may be so formed between the first pair of voltage electrodes that the contact surface space is reduced.

The housing may be so shaped and sized that a user can hold it with one hand while applying the contact surface to the one selected body region, still permitting the display to remain in sight.

The grip portion may be so formed to surround the recess, thereby facilitating the holding of the housing in one hand.

The display may be so arranged that the vertical direction of the display is orthogonally traverse to the direction in which the first pairs of current and voltage electrodes are aligned side by side, thereby facilitating the seeing of the information appearing in its screen.

The arithmetic unit may further calculate at least one of body fat, body water, pulse, or blood pressure.

The alternating current supplying device may supply a plurality of alternating currents of different frequencies; the voltage measuring device may measure the voltage every time when an alternating current of selected frequency is supplied; and the arithmetic unit may calculate the bioelectrical impedance values from each alternating current and corresponding voltage.

The alternating current supplying device may supply an alternating current of a single frequency; the voltage measuring device may further measure the phase of the voltage measured by it; and the arithmetic unit may further calculate the phase difference between the phase of the supplying alternating current and the phase of the measured voltage.

The arithmetic unit may further calculate at least one of the ratio between extra-cellular water and intra-cellular water, the ratio of body water and extra-cellular water, intra-cellular water, extra-cellular water, body water, or body fat.

A bioelectrical impedance measuring apparatus according to a second aspect of the present invention comprises a rest on which one selected body region may be put; a pair of current electrodes so placed on the rest that the one selected body region may be put in contact with the current electrodes; a pair of voltage electrodes so placed on the contact surface between the pair of current electrodes that the one selected body region may be put in contact with the voltage electrodes; a position member which permits the one selected body region to be put in correct position; an alternating current supplying device which supplies the pair of current electrodes with alternating current; a voltage measuring device which measures the voltage appearing between the pair of voltage electrodes; and an arithmetic unit which calculates the bioelectrical impedance from the supplying alternating current and the measured voltage.

A bioelectrical impedance measuring apparatus according to a third aspect of the present invention comprises a rest on which one selected body region may be put; a pair of current electrodes so placed on the rest that the one selected body region may be put in contact with the current electrodes; a pair of voltage electrodes so placed on the contact surface between the pair of current electrodes that the one selected body region may be put in contact with the voltage electrodes; a cover member capable of pushing the one selected body region against the two pairs of electrodes; an alternating current supplying device which supplies the pair of current electrodes with alternating current; a voltage measuring device which measures the voltage appearing between the pair of voltage electrodes; and an arithmetic unit which calculates the bioelectrical impedance from the supplying alternating current and the measured voltage.

A bioelectrical impedance measuring apparatus according to a fourth aspect of the present invention comprises a rest on which one selected body region may be put; a cover member so pivotally fixed to one longitudinal edge of the rest that the one selected body region may be sandwiched between the rest and the cover member which is put in its closed position; a pair of current electrodes and a pair of voltage electrodes so placed on the surface of the cover member to push the two pairs of electrodes against the one selected body region lying on the contact surface of the rest, the pair of voltage electrodes intervening between the pair of current electrodes; an alternating current supplying device which supplies the pair of current electrodes with alternating current; a voltage measuring device which measures the voltage appearing between the pair of voltage electrodes; and an arithmetic unit which calculates the bioelectrical impedance from the supplying alternating current and the measured voltage.

A bioelectrical impedance measuring apparatus according to a fifth aspect of the present invention comprises a housing having a contact surface to be applied to one selected body region and a grip portion, the housing having an alternating current supplying device, a voltage measuring device and an arithmetic unit equipped therewith; a pair of current electrodes so placed on the contact surface that the one selected body region may be put in contact with the current electrodes; a pair of voltage electrodes so placed on the contact surface between the pair of current electrodes that the selected one body region may be put in contact with the voltage electrodes; and a display placed on a selected place of the housing other than the contact surface; the alternating current supplying device supplying the first pair of current electrodes with alternating current; the voltage measuring device measuring the voltage appearing between the pair of voltage electrodes; the arithmetic unit calculating the bioelectrical impedance from the supplying alternating current and the measured voltage; and a recess being so formed between the first pair of voltage electrodes that the contact surface space is reduced.

Other objects and advantage of the present invention will be understood from the following description of some preferred embodiments, which are shown in accompanying drawings.

DESCRIPTION OF PREFERRED EMBODIMENTS

First Embodiment

Figure 4:
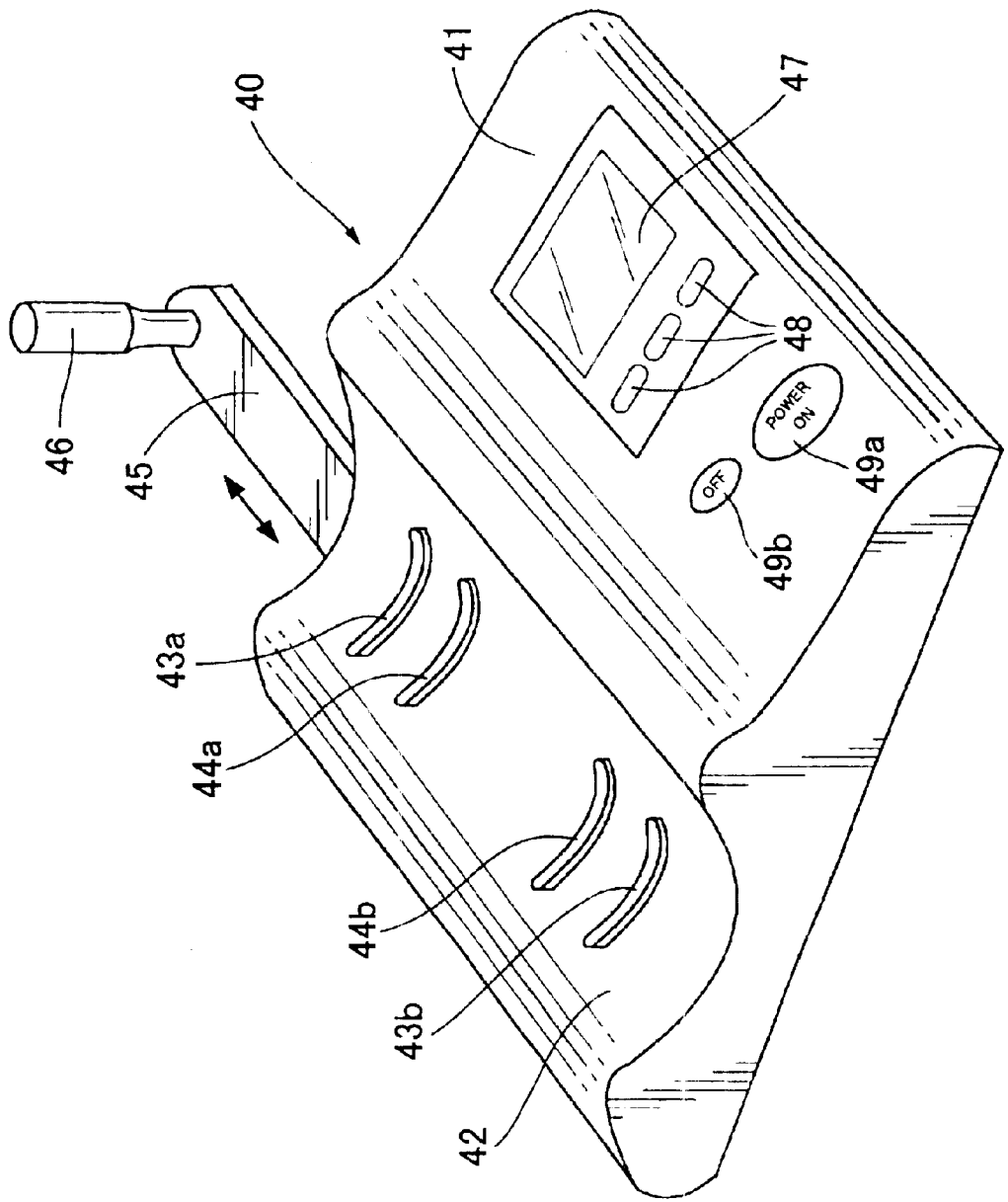
FIG. 4 shows the external appearance of a bioelectrical impedance measuring apparatus according to the first embodiment of the present invention.

FIG. 4 shows the external appearance of a bioelectrical impedance measuring apparatus according to the first embodiment as viewed from a user, showing how some parts are arranged on the top of the housing 41. The measuring apparatus 40 is designed to measure the bioelectrical impedance appearing between two points selected on the forearm. The housing 41 is of substantially rectangular-planar shape as a whole. The left side of the housing 41 comprises a forearm rest 42 extending from the front to rear side of the housing 41, and the upper surface of the forearm rest 42 looks like a semi-cylindrical trough. A current electrode 43b, a voltage electrode 44b, another voltage electrode 44a and another current electrode 43a are parallel-fixed on the semi-cylindrical surface of the trough in the order named. Each electrode 43a, 44a, 44b or 43b traverses the longitudinal direction of the forearm rest 42, and the electrode is so curved in conformity with the semi-cylindrical surface that they may be almost coplanar therewith.

An extendable slider 45 having a flat plate shape is provided on the rear side of the housing 41. The slider 45 extends in the direction in which the electrodes 43a, 44a, 44b and 43b are arranged side by side. A stick-like grip 46 stands upright from the rear end of the slider 45. The grip 46 can move back and forth an adjustable distance from the rear end of the housing 41 in the longitudinal direction of the forearm rest 42. On the right side of the housing 41 there are provided a display part 47, input keys 48, a power "ON" key 49a and a power "OFF" key 49b. The display part 47 shows some helpful guidance of operation, the progressing of measurement, the results of measurement, the results of arithmetic operation, and such like. The input keys 48 enables the user to input data such as instructions for controlling the measuring apparatus 40 and the user's personal particulars required for measurements. The power "ON" key 49a and the power "OFF" key 49b enable the user to make the measuring apparatus 40 turn on and off.

Figure 5:
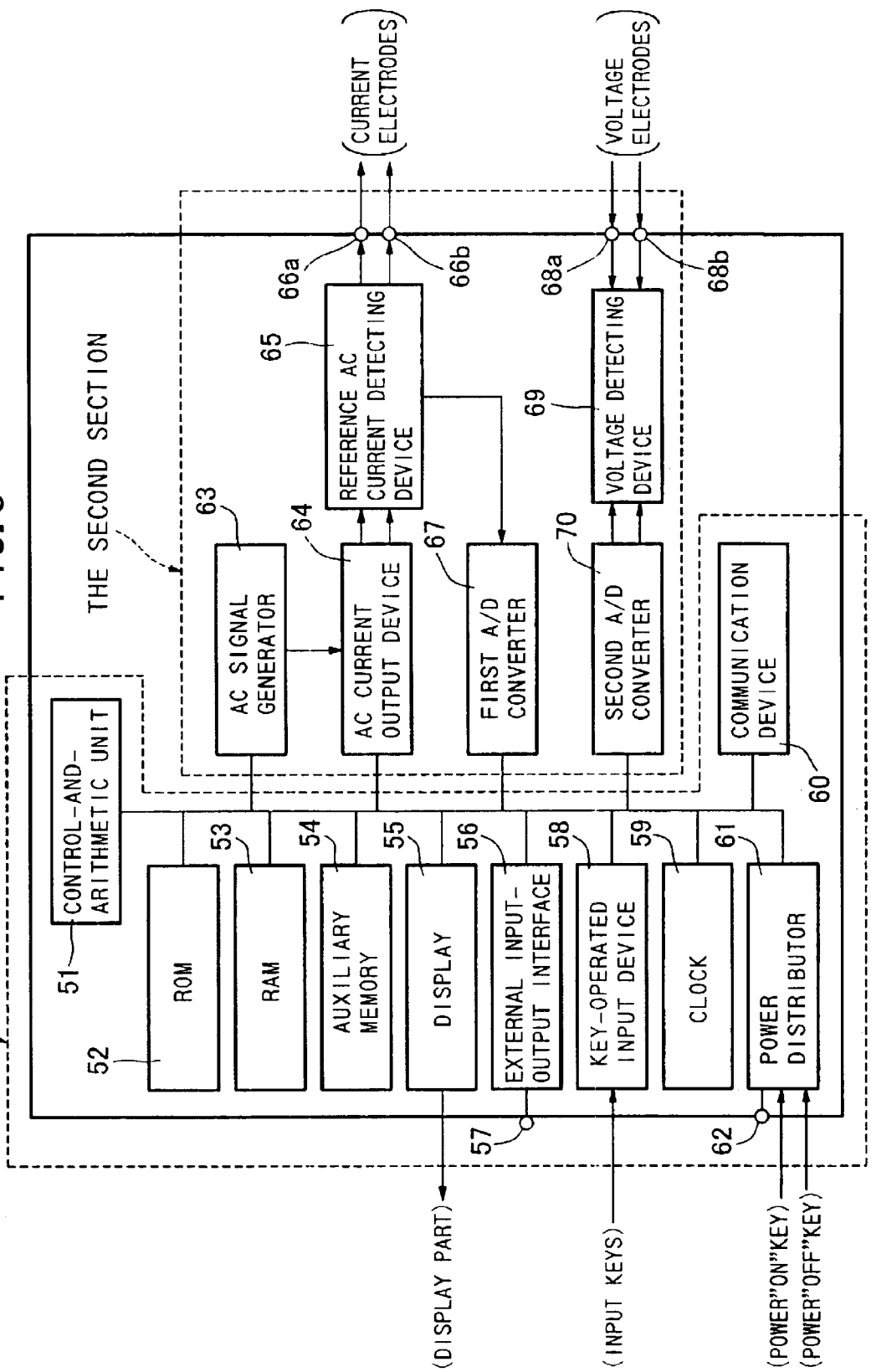
FIG. 5 illustrates the major parts installed in the housing of the bioelectrical impedance measuring apparatus of FIG. 4.

FIG. 5 illustrates the major parts installed in the housing 41 of the bioelectrical impedance measuring apparatus according to the first embodiment. As seen from the drawing, these parts are grouped in two sections (broken lines): the first section takes the roles of control, arithmetic operation, and input-output of data whereas the second section takes the roles of measurement of bioelectrical impedance and A/D conversion.

The first section includes a control-and-arithmetic unit 51, a ROM 52, a RAM 53, a nonvolatile auxiliary memory 54, a display device 55, an external input-output interface 56, an external interface terminal 57, a key-operated input device 58, a clock 59, a modem built-in communication device 60, a power distributor 61 and a power supply terminal 62.

The control-and-arithmetic unit 51 performs the controlling of measurement and the processing of the results of measurement. The ROM 52 stores programs and some parameters for control and arithmetic operations. The RAM 53 temporarily stores the results of measurement or acquired data, the results of arithmetic operations, the data derived from external devices, selected programs and such like. The auxiliary memory 54 stores the acquired data, the results of arithmetic operations, some parameters relating to measurements and such like. The display device 55 is connected to the display part 47 and shows on the display part 47 some helpful guidance of operation, the progressing of measurement, the results of measurements, the results of arithmetic operations and such like. The external input-output interface 56 permits some parameters relating to measurement and the results of measurements to be transferred to external devices, and inversely it permits some parameters relating to measurement, instructions for controlling measurement, control programs and such like to be supplied from external devices. The external input-output interface 56 can be connected to given external devices via the external interface terminal 57. The key-operated input device 58, in responsive to the depression of the input keys 48 connected thereto, inputs data such as instructions for controlling the measuring apparatus 40 and user's personal particulars required for measurement. The clock 59 measures on what day and time each measurement is made, recording such day and time for later use. The communication device 60 transmits the results of measurements and some derivations therefrom to other computers via telephone lines. The power distributor 61, in responsive to the depression of the power "ON" key 49*a* or the power "OFF" key 49*b* connected thereto, starts or stops electric power supply from an external power supply via the terminal 62 to each part of the measuring apparatus 40.

The second section includes an AC signal generator 63, an AC current output device 64, a reference AC current detecting device 65, paired AC current output terminals 66*a* and 66*b* connected to the paired current electrodes 43*a* and 43*b* respectively, a first A/D converter 67, the paired voltage measurement terminals 68*a* and 68*b* connected to the paired voltage electrodes 44*a* and 44*b* respectively, a voltage detecting device 69 and a second A/D converter 70.

The AC signal generator 63 provides a plurality of alternating current signals of different frequencies which are determined according to the control program stored in the ROM 52 or the RAM 53. Such alternating currents of different frequencies are directed to the AC current output device 64, in which their effective values are modified according to the control program stored in the ROM 52 or the RAM 53, and then the so modified alternating currents are directed to the reference AC current detecting device 65. The device 65 provides the alternating currents of different frequencies sequentially at its output terminals 66*a* and 66*b*, so that a selected alternating current may be made to flow in one's body via the paired current electrodes 43*a* and 43*b*. At the same time the device 65 detects the quantity of the alternating current flowing in the body, the analogue value of which alternating current is converted to a corresponding digital value in the first A/D converter 67. On the other hand the voltage detecting device 69 receives at its input terminals 68*a* and 68*b* a signal representing the voltage appearing between the paired voltage electrodes 44*a* and 44*b*, which are applied to two points selected on the body. Thus, the voltage is detected in the voltage detecting device 69, and the so detected voltage is converted to a corresponding digital value in the second A/D converter 70.

Figure 6:
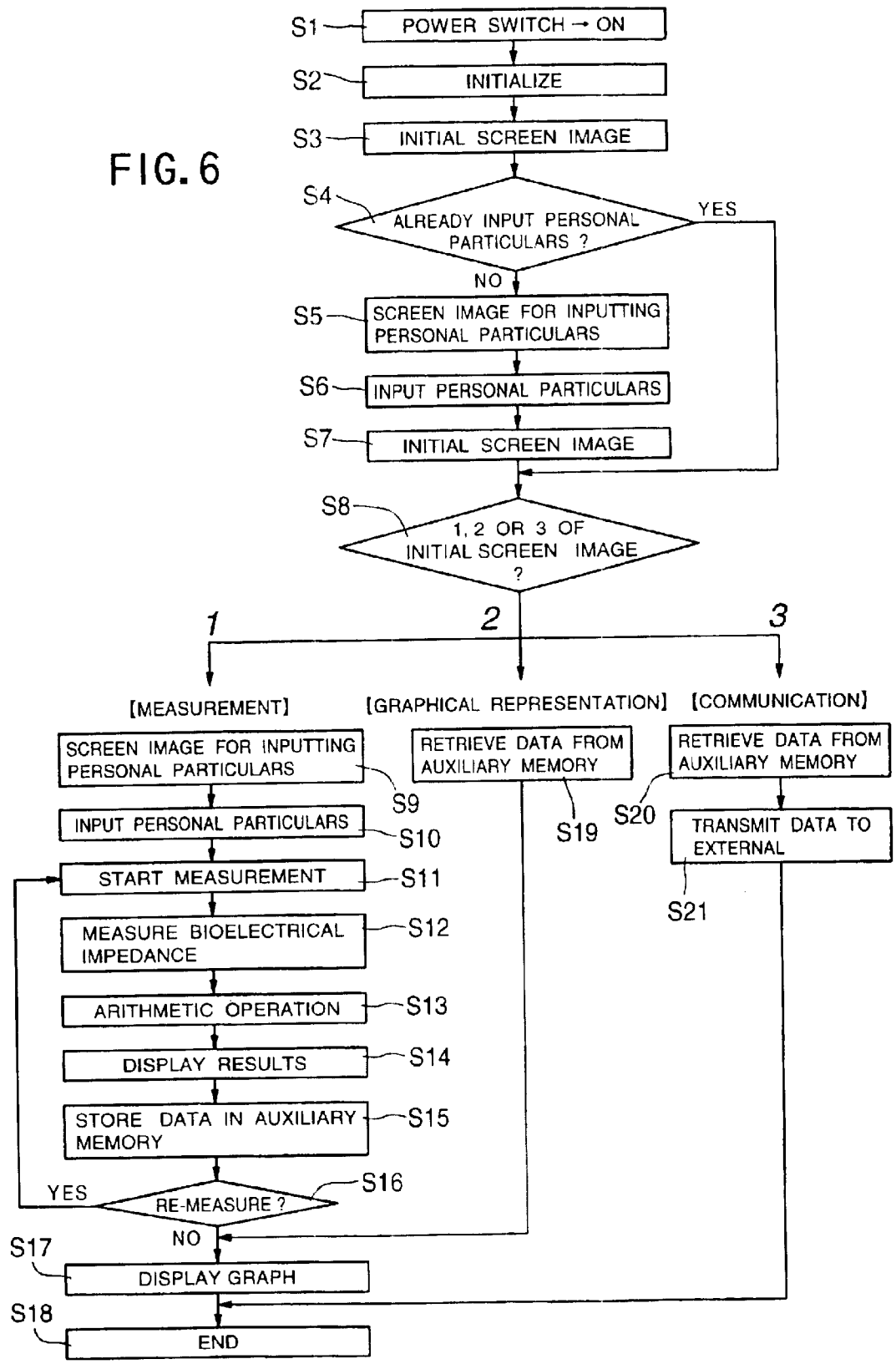
FIG. 6 is a flow chart showing a series of actions taken for measuring the bioelectrical impedance with the bioelectrical impedance measuring apparatus of FIG. 4.

FIG. 6 shows a flow chart illustrating a series of actions taken for measuring the bioelectrical impedance with the measuring apparatus shown in FIG. 4. A user depresses the power "ON" key 49*a* at step 1, thus initializing the measuring apparatus 40 at step 2. Then, the initial screen image of FIG. 7 appears on the display part 47 at step 3. At step 4 a check is made on whether the user's personal particulars including sex, height, weight, age have been already inputted. In the affirmative case, the proceeding goes to step 8. In the negative case the proceeding goes to step 5, at which a blanked screen image for inputting user's personal particulars appear on the display part 47. Immediately after the user fills the blanks with his personal particulars by depressing the input keys 48 at step 6, the initial screen image appears on the display part 47 again at step 7, and then the proceeding goes to step 8.

Figure 7:
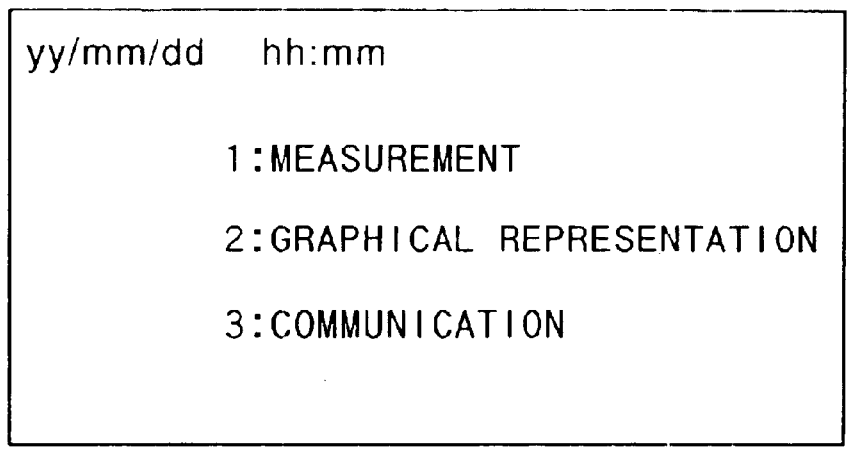
FIG. 7 illustrates an initial screen image initially appearing in the display of the bioelectrical impedance measuring apparatus of FIG. 4.

At step 8 the user can select a desired item among "measurement", "graphical representation" and "communication" simply by depressing the input keys 48 to input "1", "2" or "3" allotted to such functions appearing in the screen image of FIG. 7. Specifically when the user selects the number "1" to put the whole apparatus to stand by for measurement, the screen image having blanks filled with user's personal particulars appears for confirmation at step 9, thus allowing the user to make some modification on selected personal particulars, if necessary at step 10. Then the proceeding goes to step 11, at which the user puts the whole apparatus in front of him with the forearm rest 42 on his left side, and then he puts his forearm on the forearm rest 42 while fitting the extendable length of the slider 45 to his forearm length. In this position his forearm is put in contact with the two pairs of electrodes 43*a*, 44*a*, 44*b* and 43*b* while holding the grip 46 in his hand. Either forearm may be put on the forearm rest 42 for measurement although the left forearm is convenient; the user can use his right hand while depressing the input keys 48 on the right side. Now, the user depresses the input keys 48 to start the measurement.

The upper surface of the forearm rest 42 is like a semi-cylindrical trough, and the electrodes are so curved that they may be almost coplanar with the semi-cylindrical surface, thereby allowing the forearm to be put in close contact with the electrodes 43*a*, 44*a*, 44*b*, 43*b*. Further, the grip 46 has the effect of orienting and keeping the forearm in correct position while effecting a required measurement. This assures that the forearm may take same position at each and every occurrence of measurement.

Putting the forearm on the forearm rest 42 permits the forearm to be put in contact with the electrodes 43*a*, 44*a*, 44*b*, 43*b*, which eliminates the inconveniences of handling elongated cables and applying electrodes to the forearm in making a required measurement. Thus, the measuring apparatus 40 is very convenient to use.

At step 12 the bioelectrical impedance is measured as follows. The AC signal generator 63 produces automatically an alternating current signal having a frequency determined in terms of some measurement parameters. These parameters are pre-stored in the ROM 52, or are stored in the RAM 53 after being transferred from the auxiliary memory 54 or the external input-output interface 56. The alternating current of the so determined frequency is directed to the AC current output device 64, where the effective value of the alternating current is modified according to similar measurement parameters. The so controlled alternating current passes through the reference AC current detecting device 65, the paired AC current output terminals 66*a* and 66*b* and the paired current electrodes 43*a* and 43*b*, flowing in the body. Then, the quantity of the alternating current flowing in the body is detected by the reference AC current detecting device 65, the analog value of which alternating current is converted to a corresponding digital value in the first A/D converter 67. The digital value is stored in the RAM 53.

On the other hand, a signal representing the voltage appearing between the paired voltage electrodes 44*a* and 44b, which are applied to two points selected on the body, is supplied to the voltage detecting device 69 via the paired voltage measurement terminals 68a and 68b. In the device 69 the voltage appearing between the paired voltage electrodes 44a and 44b is detected, and the so detected voltage is converted to a corresponding digital value in the second A/D converter 70, so that the digital value is stored in the RAM 53. The arithmetic-and-control unit 51 calculates the bioelectrical impedance based on the digital values from the first and second A/D converters 67 and 70. Repeating the above mentioned procedure, a series of bioelectrical impedance values are measured by using alternating currents of different frequencies Fi (i=1, 2, . . . , n) one after another.

Now, the proceeding goes to step 13, in which arithmetic operations using the bioelectrical impedance values measured at step 12 are executed to calculate an equation representing a locus of bioelectrical impedance vectors, which locus is drawn by plotting their points, and some variables relating to the so calculated locus.

Figure 8:
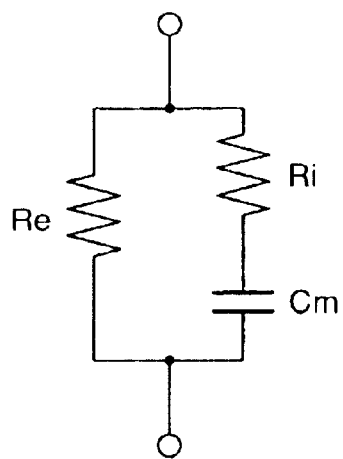
FIG. 8 shows an equivalent circuit representing bioelectrical impedance.

Ordinarily a bioelectrical impedance can be expressed equivalently by a lumped-constant circuit, which consists of extra-cellular water resistance Re, intra-cellular water resistance Ri, and cell membrane capacitance Cm as shown in FIG. 8. The locus of bioelectrical impedance values actually measured, however, is not in conformity with a semicircular locus drawn theoretically from the impedance values, which are determined from the equivalent circuit whose components are given in the form of lumped constant elements. Because all cells of a living body cannot be expressed by one and same equivalent circuit; specifically each cell has a different shape and characteristic, and should be expressed by a different equivalent circuit allotted only to the same, particular cell for exclusive use. As a matter of fact, the locus of bioelectrical impedance vectors actually measured is given by an arc determined according to Cole-Cole model.

Figure 9:
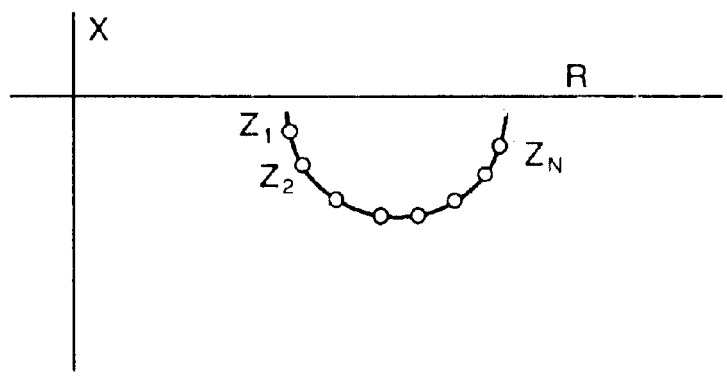
FIG. 9 shows one example of locus which the points of bioelectrical impedance vectors follow.

One example of arc-like locus determined from Cole-Cole model is shown in FIG. 9, in which the abscissa (X-axis) and the ordinate (Y-axis) represent the resistive component and reactive component of the bioelectrical impedance respectively. As the reactive component of the bioelectrical impedance is capacitive, and is given by a negative value, the locus of bioelectrical impedance is located below the X-axis. As the calculated locus of bioelectrical impedance is assumed to be in conformity with circular arc shape, the points of bioelectrical impedance $Z_1, Z_2, \ldots, Z_N$ actually measured in terms of frequencies $F_1, F_2, \ldots, F_N$ follow a selected part of the circumference of a circle, which is given by the following equation (1):

$$(X-a)^2+(Y-b)^2=r^2 \quad (1)$$

where "a" and "b" are the abscissa and ordinate of the center of the circle, and "r" stands for the radius of the circle. The values of "a", "b" and "r" can be given by putting the impedance values $Z_1, Z_2, \ldots, Z_N$ actually measured in terms of frequencies $F_1, F_2, \ldots, F_N$ in equation (1).

Equation (1) is rewritten in terms of "X":

$$X=a\pm\sqrt{r^2-b^2} \quad (2)$$

The X-axis traverses the circle represented by equation (1) at the intersections R0 and Rinf (R0>Rinf), which intersections can be given by equations (3) and (4):

$$R0=a+\sqrt{r^2-b^2} \quad (3)$$

$$Rinf=a-\sqrt{r^2-b^2} \quad (4)$$

Re and Ri of an equivalent circuit in FIG. 8 can be given by equations (5) and (6):

$$Re=R0 \quad (5)$$

$$Ri=R0 \cdot Rinf/(R0-Rinf) \quad (6)$$

The characteristic bioelectrical impedance vector Zc appears in measurement by making an alternating current of characteristic frequency Fc to flow in the body. Its reactive component has a maximum absolute value on the locus of bioelectrical impedance. The abscissa and ordinate of the characteristic bioelectrical impedance are given by:

$$X=a \quad (7)$$

$$Y=b-r \quad (8)$$

Zc is represented by equation (9):

$$Zc=Rc+jXc=a+j(b-r), \quad (9)$$

where Rc and Xc stand for the resistive and reactive components of Zc.

Bioelectrical impedance vectors for given angular frequencies ω can be calculated on the basis of Cole-Cole model, and are given by equation (10):

$$Z(\omega) = \frac{R0 - Rinf}{1 + (j\omega\tau)^\beta}, \quad (10)$$

where Z(ω) stands for bioelectrical impedance vector for ω; and τ and β are constants. Following equation (11) results by putting 1/ωc as a substitute for τ in equation (10):

$$Z(\omega) = \frac{R0 - Rinf}{1 + (j\omega/\omega_c)^\beta}, \quad (11)$$

where ω c is equal to 2πFc. Fc and β can be calculated from equation (11) by using the measured value of bioelectrical impedance.

From the equation of the bioelectrical impedance locus, and from the derivations from measured values of bioelectrical impedance, such as R0, Rinf, Re, Ri, Zc, Rc, Xc, Fc, and such like, the weight each of following body compositions can be calculated: extra-cellular water, intra-cellular water, total body water (a sum of extra-cellular water plus intra-cellular water), body fat, fat free mass (which can be obtained by subtracting the body fat from the body weight) and such like. Further, from these calculated composition weights, following variables can be obtained: a ratio between intra-cellular water and extra-cellular water, a ratio between extra-cellular water and total body water, the state of thirst of body (which can be determined from total body water percentage), body fat percentage and such like.

Then the proceeding goes to step 14, where the measured values and the derivations therefrom appears on the display part 47. At step 15 the measured values and the derivations therefrom may be stored in the auxiliary memory 54 or such data may be transferred to external devices via the external input-output interface 56. Then at step 16, where if the user inputs a re-measuring command by depressing the input keys 48, the proceeding goes back to step 11, from which another series of actions taken for measurement are executed again. If the user inputs a graphic representation command instead of the re-measuring command by depressing the input keys 48, the proceeding goes to step 17, where the retro-graphic representation of the values measured before and the derivations therefrom appears on the display part 47. At step 18, the depression of the power "OFF" key 49b makes the measuring apparatus 40 turn off, finishing the measurement.

The following description returns to and begins with step 8. At step 8 when the user inputs the number "2" allotted to "graphical representation" by depressing the input keys 48, the proceeding goes to step 19, where selected data and parameters for display are retrieved from the auxiliary memory 54. Then, at step 17 as described above the predetermined data appears on the display part 47. At step 18 as described above the depression of the power "OFF" key 49b makes the measuring apparatus 40 turn off, finishing the measurement.

Likewise, at step 8 when the user inputs the number "3" allotted to "communication" by depressing the input keys 48, the proceeding goes to step 20, where selected data and parameters are retrieved from the auxiliary memory 54. At step 21, these data and parameters are transmitted to a selected external data processor via telephone lines. Such data may include: the values of bioelectrical impedance and other measured values (voltage, phase difference therebetween, and date and time of measurement, etc.); derivations therefrom (R0, Rinf, Re, Ri, Zc, Rc, Xc, or Fc, etc.); weights of body compositions (intra-cellular water, extra-cellular water, total body water, fat free mass or body fat, etc.); a variety of index values of edema (extra-cellular water, ratio between intra-cellular water and extra-cellular water, ratio between extra-cellular water and total body water, etc.); personal particulars (identification number, name, sex, age, height, body weight, etc.) and so on. At step 18 as described above the depressions of the power OFF key 49b makes the measuring apparatus 40 turn off, finishing the measurement.

Instead of measuring the bioelectrical impedance in terms of alternating currents of a plurality of frequencies at the steps 12 and 13 as described above, the bioelectrical impedance may be simply measured in terms of an alternating current of a single frequency. In that case, at step 12, an alternating current of single frequency $F_1$ in place of the plurality of frequencies is made to flow in the body to measure the bioelectrical impedance value and the phase difference between the applied alternating current and the measured voltage appearing between two points selected on the body.

Figure 10:
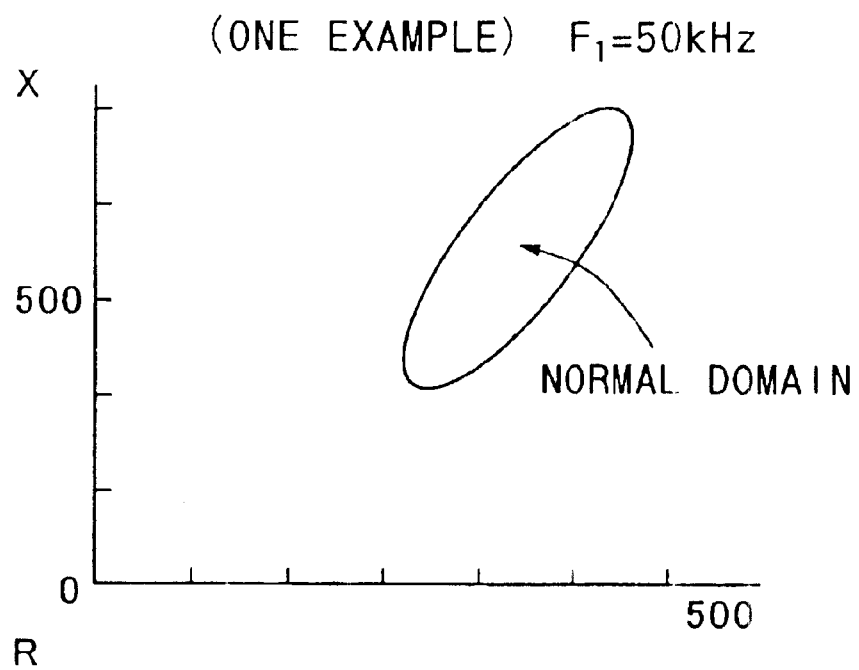
FIG. 10 shows a certain domain in which normal values of bioelectrical impedance can be given in terms of resistive and reactive components.

At step 13 a decision is made on the bioelectrical impedance value $Z_1$ measured for the frequency $F_1$ in terms of whether it is in a normal impedance domain (see the graph of FIG. 10 plotted for 50 KHz, abscissa: resistive value R and ordinate: reactive value X), in which normal values of bioelectrical impedance would exist. If the bioelectrical impedance value $Z_1$ is not within the domain, it is supposed to be abnormal, and then, some variables relating to the locus of bioelectrical impedance vectors are obtained from the measured value of bioelectrical impedance as follows.

Figure 11:
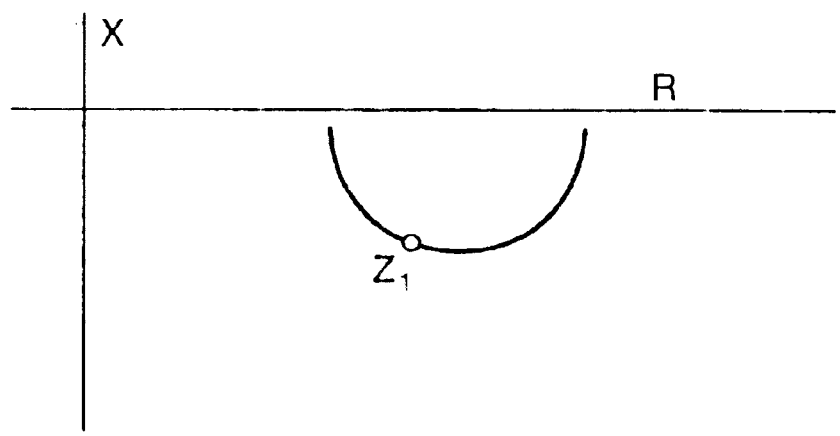
FIG. 11 shows one example of locus which the points of bioelectrical impedance vectors follow.

As described the above, the locus of bioelectrical impedance vectors actually measured is assumed to be in conformity with circular arc shape. The bioelectrical impedance $Z_1$ is located on a selected point of the circumference of the circle as shown in FIG. 11, in which the abscissa (X-axis) and the ordinate (Y-axis) represent the resistive component and reactive component of the bioelectrical impedance respectively.

A bioelectrical impedance value for a given angular frequency ωF is given by:

$$Z(\omega F) = \frac{1}{1 + (j\omega F/\omega 0)^\beta}, \quad (12)$$

where ω0 and β are constants. Following equation (13) results by substituting 1 for β in equation (12):

$$Z(\omega F) = \frac{1}{1 + j\omega F/\omega 0} \quad (13)$$

From the measured value of bioelectrical impedance, the measured phase difference and resistive value calculated on the basis of the measured voltage and applied current, the weights of body compositions such as total body water, fat free mass, body fat, and such like can be calculated. From these calculated composition weights, variables such as body fat percentage can be obtained.

Second Embodiment

Figure 12:
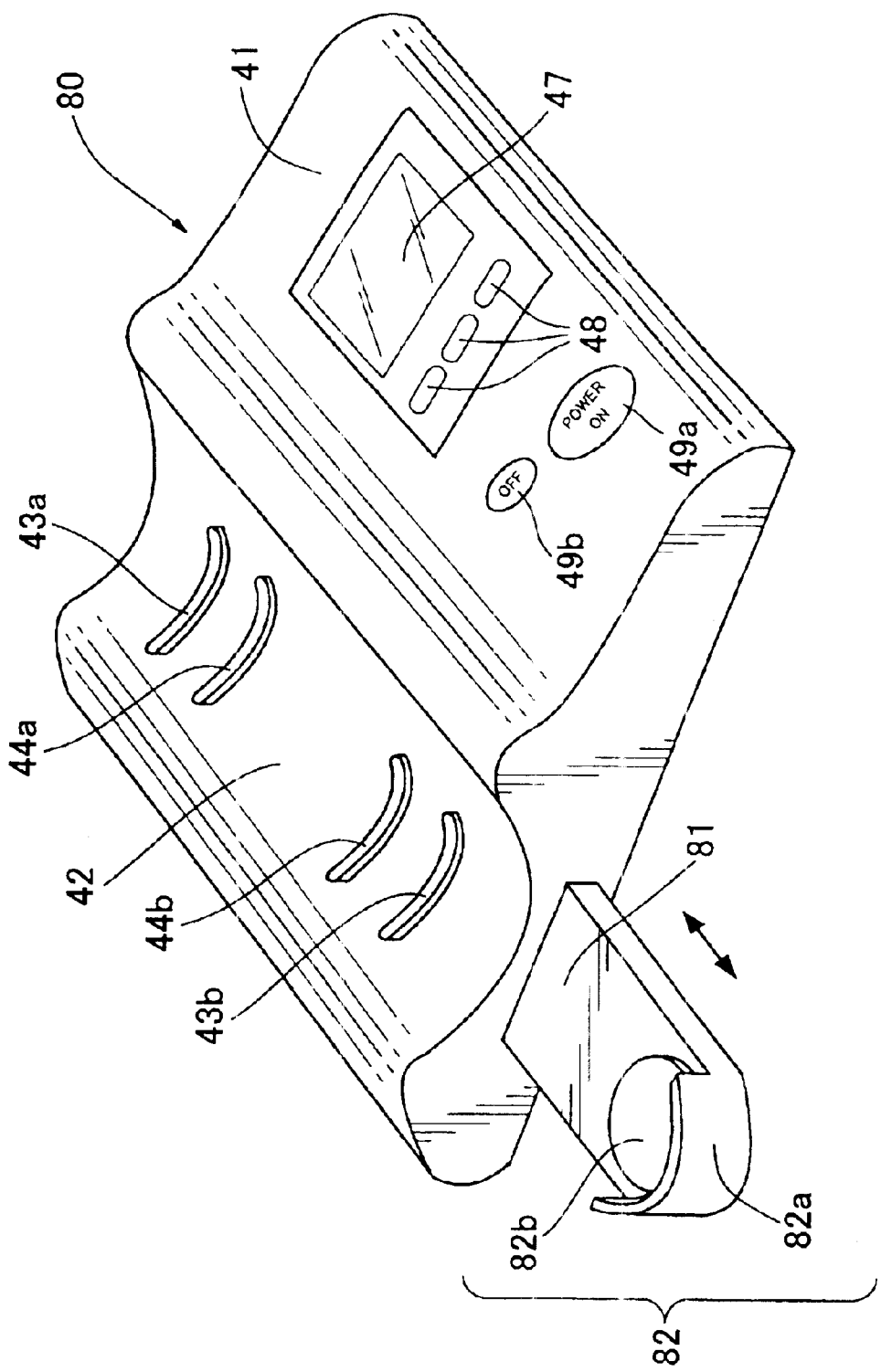
FIG. 12 shows the external appearance of a bioelectrical impedance measuring apparatus according to the second embodiment of the present invention.

FIG. 12 illustrates the external appearance of a bioelectrical impedance measuring apparatus according to the second embodiment as viewed from a user. In the drawing, the same parts as those shown in FIG. 4 are indicated by the same reference numerals. This measuring apparatus 80 is designed to measure the bioelectrical impedance appearing between two points selected on the forearm as in the aforementioned first embodiment. As shown in FIG. 12, an extendable slider 81 having a flat plate for elbow rest 82 is provided on the front side of the housing 41 as a substitute for the forearm slider 45 of the first embodiment. The slider 81 extends in the direction in which the electrodes 43a, 44a, 44b and 43b are arranged side by side. The elbow rest 82 in this particular embodiment takes the role of the stick-like grip 46 in the extendable slider 45 in the first embodiment. The elbow rest 82 comprises elbow-application piece 82a integrally connected to the semicircular end of the flat plate 81 and a circular elbow pad 82b laid in the vicinity of the elbow-application piece 82a. The elbow rest 82 can move back and forth to be an adjustable distance apart from the front end of the housing 41 in the longitudinal direction of the forearm rest 42. The other parts arranged on the surface of the housing 41 are same as those of the first embodiment (see FIG. 4).

The major parts installed in the housing 41 are same as those of the first embodiment (see FIG. 5).

In this particular embodiment, the series of actions taken for measuring the bioelectrical impedance are similar to those in the first embodiment (see FIG. 6) except for step 11, which is modified as follows: the user puts his forearm on the forearm rest 42 while fitting the extendable length of the slider 81 to his forearm length. In this position his forearm is put in contact with the electrodes 43a, 44a, 44b and 43b with his elbow applied to the elbow application piece 82a and the elbow pad 82b. As may be realized, the elbow rest 82 has the effect of orienting and keeping the forearm in correct position while effecting a required measurement. This assures that the forearm takes same position at each and every occurrence of measurement.

Third Embodiment

Figure 13:
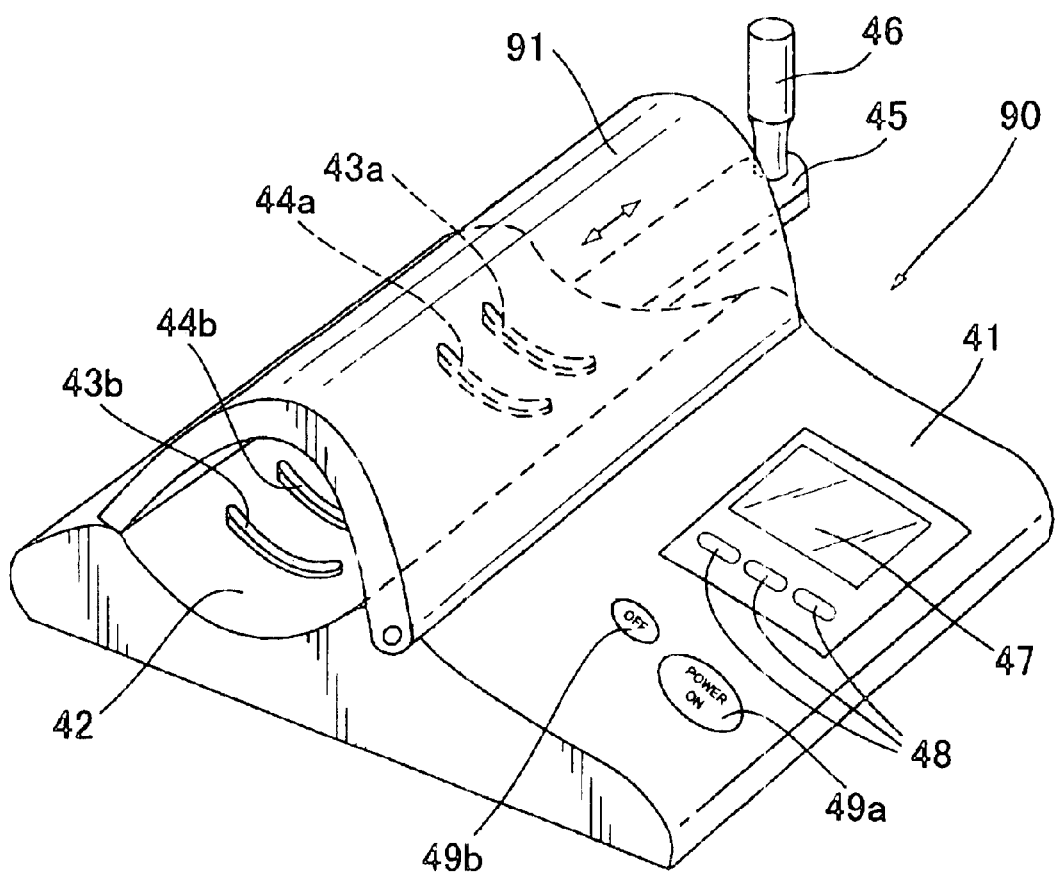
FIG. 13 shows the external appearance of a bioelectrical impedance measuring apparatus according to the third embodiment of the present invention.

FIG. 13 shows the external appearance of a bioelectrical impedance measuring apparatus according to the third embodiment as viewed form a user. In the drawing, the same parts as those of the first embodiment are identified by the same reference numerals (see FIG. 4). This measuring apparatus 90 is also designed to measure the bioelectrical impedance appearing two points selected on the forearm as in the aforementioned first embodiment. The measuring apparatus 90 is a modification of first embodiment of FIG. 4, which additionally includes a cover member 91. The cover member 91 is pivotally fixed to one longitudinal edge of the forearm rest 42, looking like a semi-cylindrical dome in its closed position and extending in the direction in which the electrodes 43a, 44a, 44b and 43b are arranged side by side. Preferably the cover member 91 can be rotated about its pivot axle with counter friction large enough to cause the user to feel some pleasing resistance when he raises his forearm. The other parts arranged on the surface of the housing 41 are same as those of the first embodiment (see FIG. 4).

The major parts installed in the housing 41 of the measuring apparatus 90 are same as those of the first embodiment (see FIG. 5).

In this particular embodiment, the series of actions taken for measuring the bioelectrical impedance of this embodiment are similar to those of the aforementioned first embodiment (see FIG. 6), except for step 11. At step 11 the user puts the whole apparatus in front of him with the forearm rest 42 on his left side. Then, he opens the cover member 91 pivotally and puts his forearm on the forearm rest 42 while fitting the extendable length of the slider 45 to his forearm length. In this position his forearm is put in contact with the two pairs of electrodes 43a, 44a, 44b and 43b while holding the grip 46 in his hand. Either forearm may be put on the forearm rest 42 for measurement although the left forearm is convenient; the user can use his right hand while depressing the input keys 48, or opening or closing the cover member 91. Then, he closes the cover member to sandwich his forearm between the cover member 91 and the forearm rest 42, thus pushing his forearm lying on the forearm rest 42 against the electrodes 43a, 44a, 44b, 43b.

In this measuring apparatus 90, the upper surface of the forearm rest 42 is like a semi-cylindrical trough, and the electrodes are so curved that they may be almost coplanar with the semi-cylindrical trough like surface. The cover member 91 is provided to push his forearm lying on the forearm rest 42 to the electrodes. It can be rotated about its pivot axle with counter friction large enough to cause the user to feel some pleasing resistance when he raises his forearm. The ceiling of the cover member 91, which ceiling confronts the forearm rest 42 in its closed position, has a semi-cylindrical shape. These assures that the forearm can be put in close contact with the electrodes. The cover member 91 also has the effect of making the forearm under measurement stationary.

The grip 46 has the effect of orienting and keeping the forearm in correct position while effecting a required measurement, which assures that his forearm may take same position at each and every occurrence of measurement.

Putting the forearm on the forearm rest 42 permits the forearm to be put in contact with the electrodes 43a, 44a, 44b, 43b, which eliminates the inconveniences of handling elongated cables and applying electrodes to the forearm in making a required measurement. Thus, the measuring apparatus 90 is very convenient to use.

Fourth Embodiment

Figure 14:
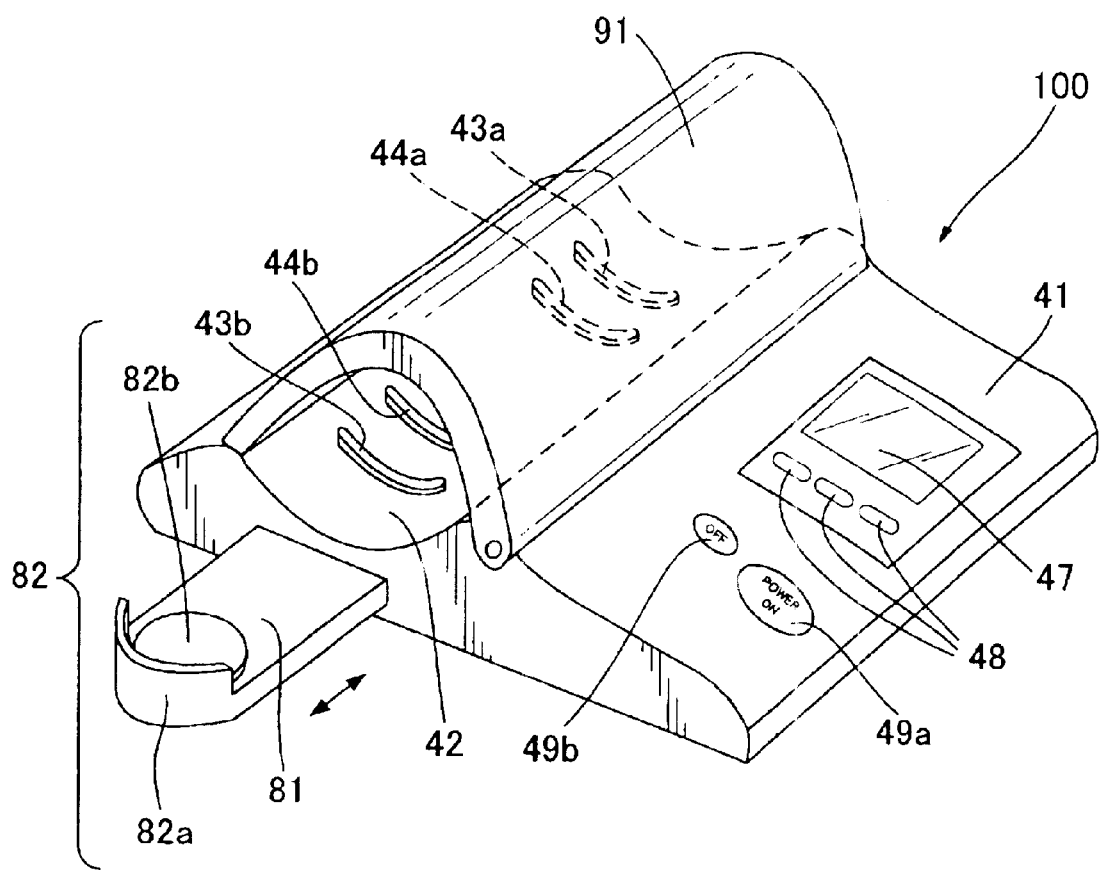
FIG. 14 shows the external appearance of a bioelectrical impedance measuring apparatus according to the forth embodiment of the present invention.

FIG. 14 shows the external appearance of a bioelectrical impedance measuring apparatus according to the forth embodiment as viewed from a user. In the drawing, the same parts as those of the second and third embodiment are identified by the same reference numerals (see FIGS. 12 and 13). The measuring apparatus 100 is also designed to measure the bioelectrical impedance appearing two points selected on the forearm as in the aforementioned first embodiment. The measuring apparatus 100 is a modification of third embodiment (see FIG. 13), which includes an extendable slider 81 and an elbow rest 82 as a substitute for the forearm slider 45 and the grip 46 of the third embodiment. The extendable slider 81 and the elbow-rest 82 are similar to those of the second embodiment (see FIG. 12). The other parts arranged on the surface of the housing 41 are same as those of the third embodiment (see FIG. 13).

The major parts installed in the housing 41 are same as those of the third (or first) embodiment (see FIG. 5).

In this particular embodiment, the series of actions taken for measuring the bioelectrical impedance of this embodiment are similar to those of the aforementioned third embodiment (see FIG. 6), except for step 11. At step 11 the user puts his forearm on the forearm rest 42 while fitting the extendable length of the slider 81 to his forearm length. In this position his forearm is put in contact with the two pairs of electrodes 43a, 44a, 44b and 43b with his elbow applied to the elbow-application piece 82a and the elbow pad 82b.

The elbow rest 82 has the effect of orienting and keeping the forearm in correct position while effecting a required measurement, which assures that the forearm may take same position at each and every occurrence of measurement.

Fifth Embodiment

Figure 15:
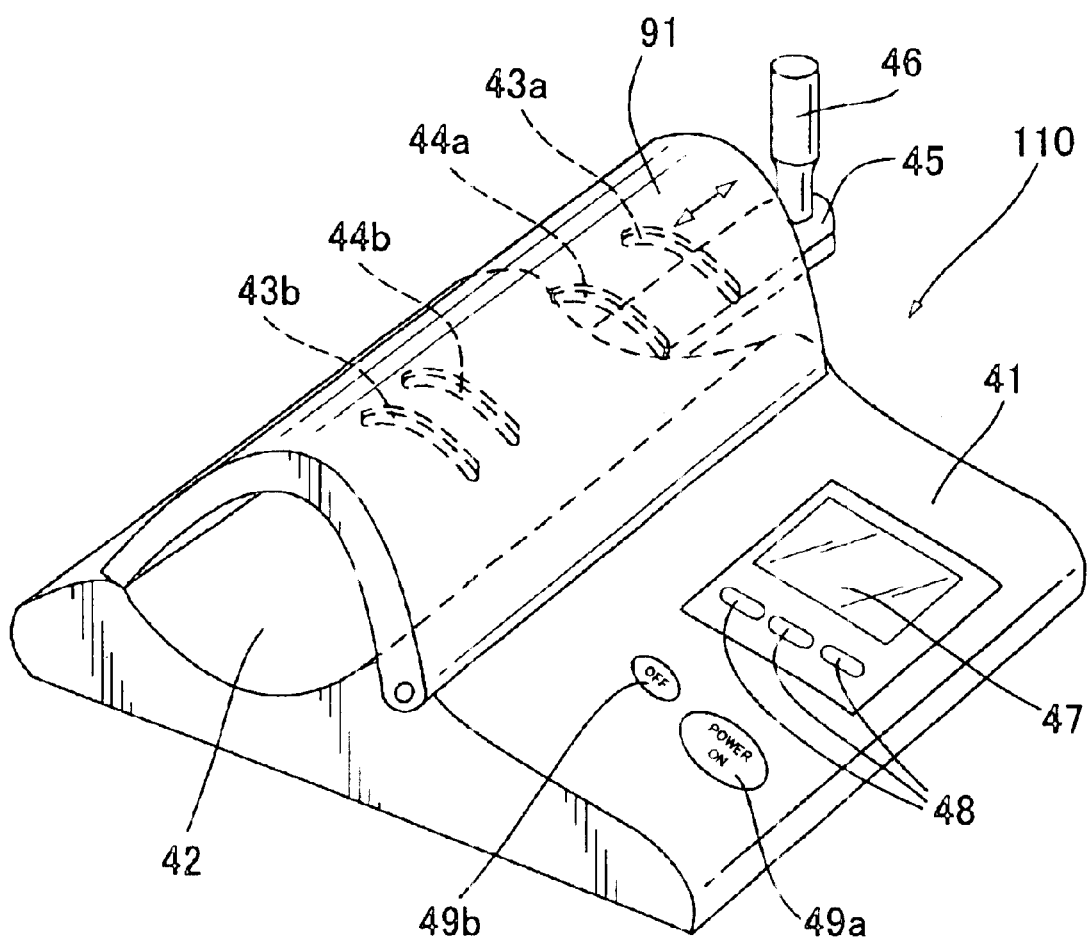
FIG. 15 shows the external appearance of a bioelectrical impedance measuring apparatus according to the fifth embodiment of the present invention.

FIG. 15 shows the external appearance of a bioelectrical impedance measuring apparatus according to the fifth embodiment as viewed from a user. In the drawing, the same parts of the third embodiment are identified by the same reference numerals (see FIG. 13). This measuring apparatus 110 is also designed to measure the bioelectrical impedance appearing two points selected on the forearm. The measuring apparatus 110 is a modification of third embodiment of FIG. 13, which has two pairs of electrodes 43a, 43b, 44a and 44b placed on the ceiling of the semi-cylindrical dome like cover member 91 in stead of the forearm rest 42. Specifically, a current electrode 43b, a voltage electrode 44b, another voltage electrode 44a and another current electrode 43a are parallel-fixed in the order named on the ceiling of the cover member 91, which ceiling confronts the forearm rest 42 when the cover member 91 is closed. Each electrode 43a, 44a, 44b or 43b traverses the longitudinal direction of the cover member 91, and the electrode is so curved in conformity with the semi-cylindrical surface that they may be almost coplanar therewith. The other parts arranged on the top surface of the housing 41 are same as those of the third embodiment (see FIG. 13).

The major parts installed in the housing 41 are same as those of the third (or first) embodiment (see FIG. 5).

In this particular embodiment, the series of actions taken for measuring the bioelectrical impedance of this embodiment are similar to those of the aforementioned third embodiment (see FIG. 6), except for step 11. At step 11 the user closes the cover member 91 pivotally to sandwich his forearm between the cover member 91 and the forearm rest 42, thus pushing the electrodes 43a, 44a, 44b, 43b against his forearm.

In this measuring apparatus 110, the ceiling of the cover member 91, which ceiling confronts the forearm rest 42 in its closed position, has a semi-cylindrical shape, and the electrodes fixed thereon are so curved that they may be almost coplanar with the semi-cylindrical dome like surface. The cover member 91 can be rotated about its pivot axle with counter friction large enough to cause the user to feel some pleasing resistance when he raises his forearm. The pushing the electrodes against his forearm with such cover member assures that his forearm can be put in close contact with the electrodes.

Sixth Embodiment

Figure 16:
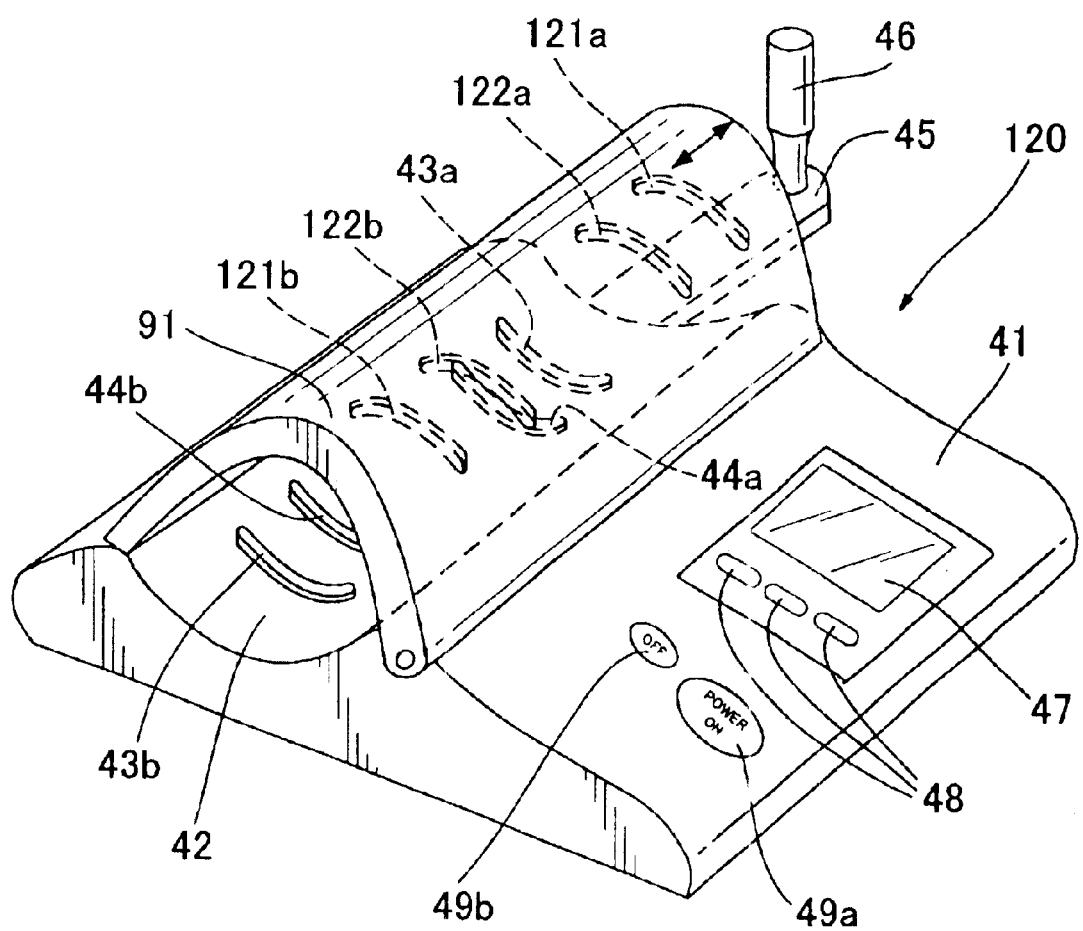
FIG. 16 shows the external appearance of a bioelectrical impedance measuring apparatus according to the sixth embodiment of the present invention.

FIG. 16 illustrates the external appearance of a bioelectrical impedance measuring apparatus according to the sixth embodiment as viewed from a user. In the drawing, the same parts as those of the third embodiment are identified by the same reference numerals (see FIG. 13). The measuring apparatus 120 is also designed to measure the bioelectrical impedance on the forearm as in the third embodiment. The measuring apparatus 120 is a modification of the third embodiment of FIG. 13, which has further paired current electrodes 121a, 121b and paired voltage electrodes 122a, 122b placed on the ceiling of the semi-cylindrical dome like cover member 91. Specifically, a current electrode 121b, a voltage electrode 122b, another voltage electrode 122a and another current electrode 121a are parallel-fixed in the order named on the ceiling of the cover member 91, which ceiling confronts the forearm rest 42 when the cover member 91 is closed. These electrodes 121b, 122b, 122a, 121a are arranged in the same order and at same intervals as the counter electrodes fixed on the forearm rest 42. Each electrode 121b, 122b, 122a, 121a traverses the longitudinal direction of the cover member 91, and the electrode is so curved in conformity with the semi-cylindrical surface that they may be almost coplanar therewith. The other parts arranged on the top surface of the housing 41 are same as those of the third embodiment (see FIG. 13).

The major parts installed in the housing 41 are similar to those of the third (or first) embodiment (see FIG. 5), although the paired AC current output terminals 66a and 66b are connected to the paired current electrodes 121a and 121b respectively. The same alternating current is supplied to the two pairs of current electrodes 121a, 121b, and 43a, 43b simultaneously, making one and the other confronting set of current electrodes 121a, 43a, and 121b, 43b to function as a single composite pair of current electrode. Accordingly, the paired voltage measurement terminals 68a and 68b are connected to the paired voltage electrodes 122a and 122b respectively. The voltage appearing between the two pairs of voltage electrodes 122a, 122b, and 44a, 44b is measured simultaneously, making one and the other confronting set of voltage electrodes 122a, 44a, and 122b, 44b to function as a single composite pair of voltage electrodes.

In this particular embodiment, the series of actions taken for measuring the bioelectrical impedance are similar to those of the third embodiment (see FIG. 6), except for steps 11 and 12. At step 11 the user closes the cover member 91 pivotally to sandwich his forearm between the cover member 91 and the forearm rest 42, thus pushing the opposite sides of the forearm against the electrodes 43a, 44a, 44b, 43b and against the electrodes 121a, 122a, 122b, 121b.

At step 12 the alternating current from the AC current output device 64 passes through the reference AC current detecting device 65, the paired AC current output terminals 66a and 66b, and the composite pair of current electrodes 121a, 43a, and 121b, 43b, flowing in the body. On the other hand, a signal representing the voltage appearing between the composite pair of voltage electrodes 122a, 44a, and 122b, 44b, which are applied to four points selected on the body, is supplied to the voltage detecting device 69 via the paired voltage measurement terminals 68a and 68b. In the device 69 the voltage appearing between the composite pair of voltage electrodes 122a, 44a, and 122b, 44b is detected, and the so detected voltage is supplied to the second A/D converter 70.

The semicircular curving of the cover member 91, the semicircular curving of the electrodes 121a, 122a, 121b, 122b, and the pleasing push of the cover member 91 against the forearm assure that the electrodes be put effectively in close contact with the forearm. Thanks to use of the composite pair of current electrodes 121a, 43a, and 121b, 43b, and the composite pair of voltage electrodes 122a, 44a, and 122b, 44b, the total electrode area to be in contact with the forearm is enlarged, thereby permitting current to flow deeply inside the forearm even if the current is of a high-frequency, and accordingly the bioelectrical impedance may be measured with accuracy.

Seventh Embodiment

Figure 17:
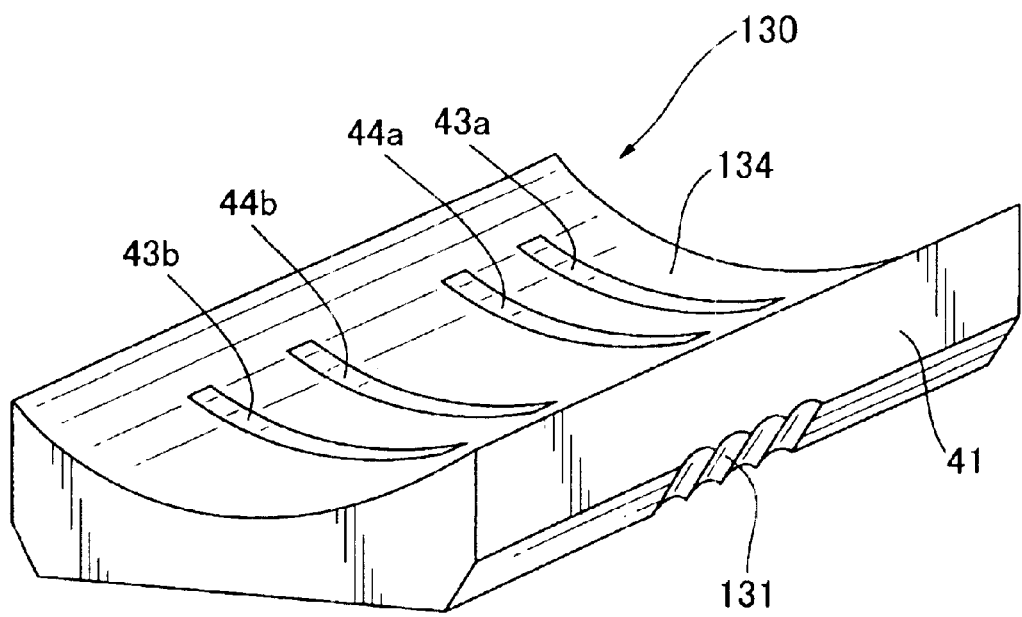
FIG. 17 shows the bottom side of a bioelectrical impedance measuring apparatus according to the seventh embodiment of the present invention.
Figure 18:
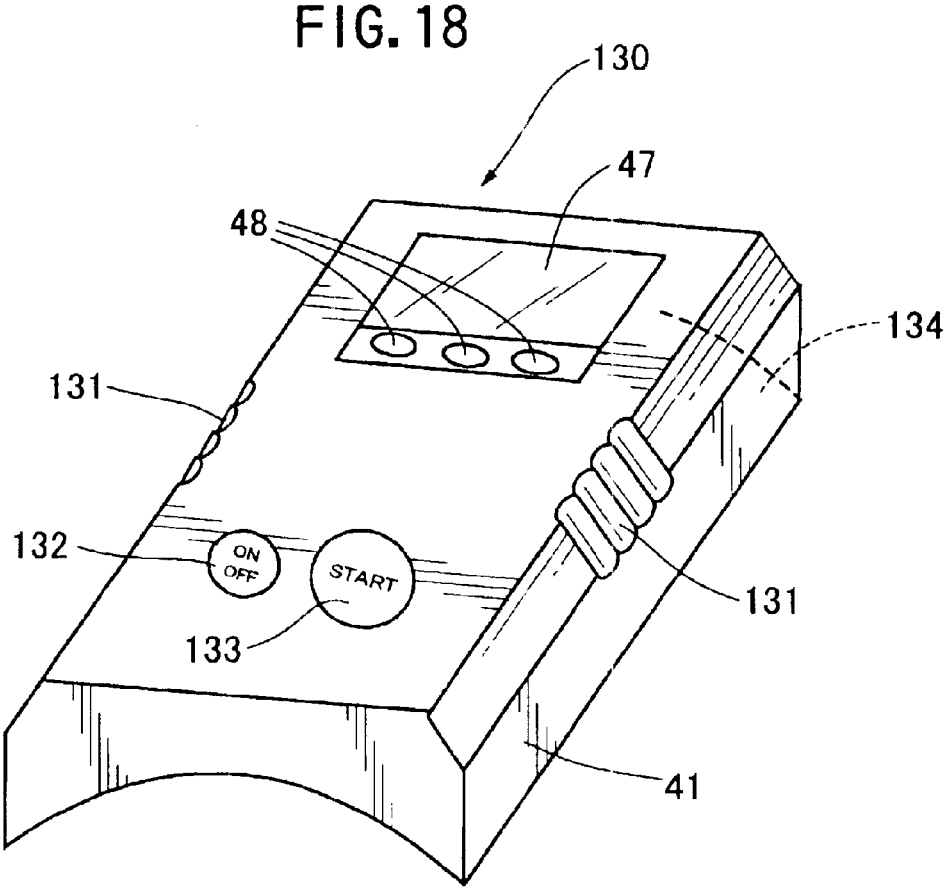
FIG. 18 shows the top side of a bioelectrical impedance measuring apparatus of FIG. 17.

FIG. 17 shows the external appearance of a bioelectrical impedance measuring apparatus according to the seventh embodiment as viewed from the bottom side thereof, showing how some parts are arranged on the bottom side of the apparatus. FIG. 18 shows the external appearance of the bioelectrical impedance measuring apparatus of FIG. 17 as viewed from the top side thereof, showing how some parts are arranged on the top side of the apparatus. In these drawings, the same parts as those of the first embodiment are identified by the same reference numerals (see FIG. 4). The measuring apparatus 130 is also designed to measure the bioelectrical impedance appearing between two selected points on the forearm. It is as large as the palm, permitting the user to hold it in one hand easily. It comprises the housing 41 which is of substantially rectangular-planar shape as a whole.

As shown in FIG. 17, the bottom side of the housing 41 is a contact surface 134 to be applied to the forearm and looks like a semi-cylindrical trough extending from the front to rear side of the housing 41 in the Figure. A current electrode 43b, a voltage electrode 44b, another voltage electrode 44a and another current electrode 43a are parallel-fixed on the semi-cylindrical contact surface 134 in the order named. Each electrode 43a, 44a, 44b or 43b traverses the longitudinal direction of the forearm rest 42, and the electrode is so curved in conformity with the semi-cylindrical surface that they may be almost coplanar therewith.

As shown in FIG. 18, on the top side of the housing 41 there are provided a display part 47, input keys 48 including a measurement start key 133, and a power "ON/OFF" key 132. The display part 47 shows some helpful guidance of operation, the progressing of measurement, the results of measurement, the results of arithmetic operation, and such like. The input keys 48 enables the user to input data such as instructions for controlling the measuring apparatus 130 and user's personal particulars required for measurements. Specifically the measurement start key 133 enables the user to input a command to start a required measurement. The power "ON/OFF" key 132, which corresponds to the power "ON" and "OFF" keys 49a, 49b of the first embodiment, enables the user to make the measuring apparatus 130 turn on and off.

Both corners of the top of the housing 41 extending in the longitudinal direction of the housing 41 are chamfered. Four indentations 131 are formed on these chamfered surfaces to align in the longitudinal direction of the housing 41. Each indentation traverses the longitudinal direction of the housing 41.

The major parts installed in the housing 41 are same as those of the first embodiment (see FIG. 5).

The series of actions taken for measuring the bioelectrical impedance of this embodiment are similar to those of the first embodiment (see FIG. 6), except for step 11. At step 11, a user holds the measuring apparatus 130 in one hand, placing his fingers on the indentations 131. Then, he applies the contact surface 134 to his forearm to put the electrodes 43a, 44a, 44b, 43b in contact with his forearm. The measurement starts when he depresses the measurement start key 133 to input a command for starting the measurement.

The contact surface 134 is like a semi-cylindrical trough, and the electrodes are so curved that they may be almost coplanar with the semi-cylindrical surface, thereby allowing his forearm to be put in close contact with the electrodes 43a, 44a, 44b, 43b.

The measuring apparatus 130 is as large as the palm as a whole, permitting the user to hold it in one hand easily, and the indentations 131 for fingers facilitates the holding of the measuring apparatus 130 in one hand. In making a required measurement it suffices that the measuring apparatus 130 be applied to one selected body region such as forearm. For these reasons a person who cares for disabled or sick people or children can conveniently use the measuring apparatus to make required measurements for them.

Putting the forearm on the forearm rest 42 permits the forearm to be put in contact with the electrodes 43a, 44a, 44b, 43b, which eliminates the inconveniences of handling elongated cables and applying electrodes to the forearm in making a required measurement. Thus, the measuring apparatus 130 is very convenient to use.

Eighth Embodiment

Figure 19:
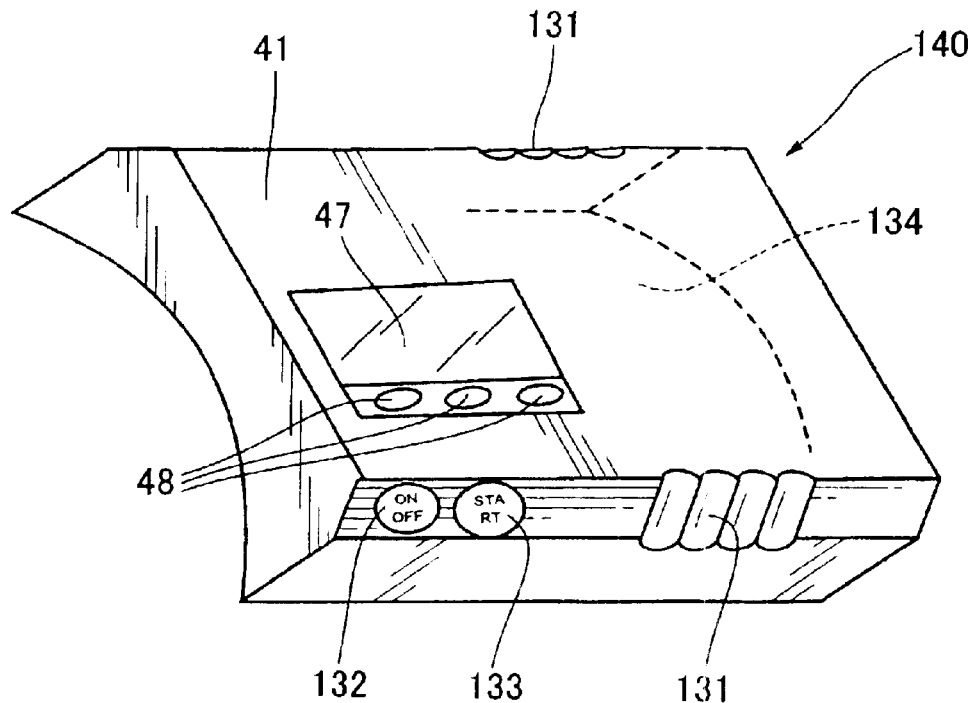
FIG. 19 shows the external appearance of a bioelectrical impedance measuring apparatus according to the eighth embodiment of the present invention.

FIG. 19 illustrates the external appearance of a bioelectrical impedance measuring apparatus according to the eighth embodiment as viewed from the top side thereof. In the drawing, the same parts as those of seventh embodiment are identified by the same reference numerals (see FIGS. 17 and 18). This measuring apparatus 140 is also designed to measure the bioelectrical impedance on the forearm as in the aforementioned seventh embodiment. The measuring apparatus 140 is a modification of seventh embodiment of FIGS. 17 and 18; the arrangement of a display 47, a measuring start key 133 and a power "ON/OFF" key 132 are modified. The display part 47 of this measuring apparatus 140 is so arranged that the vertical direction of the display part 47 is orthogonally traverse to the longitudinal direction of the contact surface 134. Such arrangement of the display part 47 facilitates the seeing of the information appearing on the display part 47 by the user thereof while the measuring apparatus 140 is being held in one hand by the user and applied to the other forearm. The measuring start key 133 and the power "ON/OFF" key 132 are arranged on one of the chamfered surfaces. Such arrangement of these keys facilitates the depression of these keys with fingers while holding the measuring apparatus 140 in one hand. The other external parts of the measuring apparatus 140 are same as those of the seventh embodiment (see FIGS. 17 and 18).

The major parts installed in the housing 41 are same as those of the seventh (or first) embodiment (see FIG. 5).

The series of actions taken for measuring the bioelectrical impedance of this embodiment are similar to those of the seventh embodiment (see FIG. 6).

Ninth Embodiment

Figure 20:
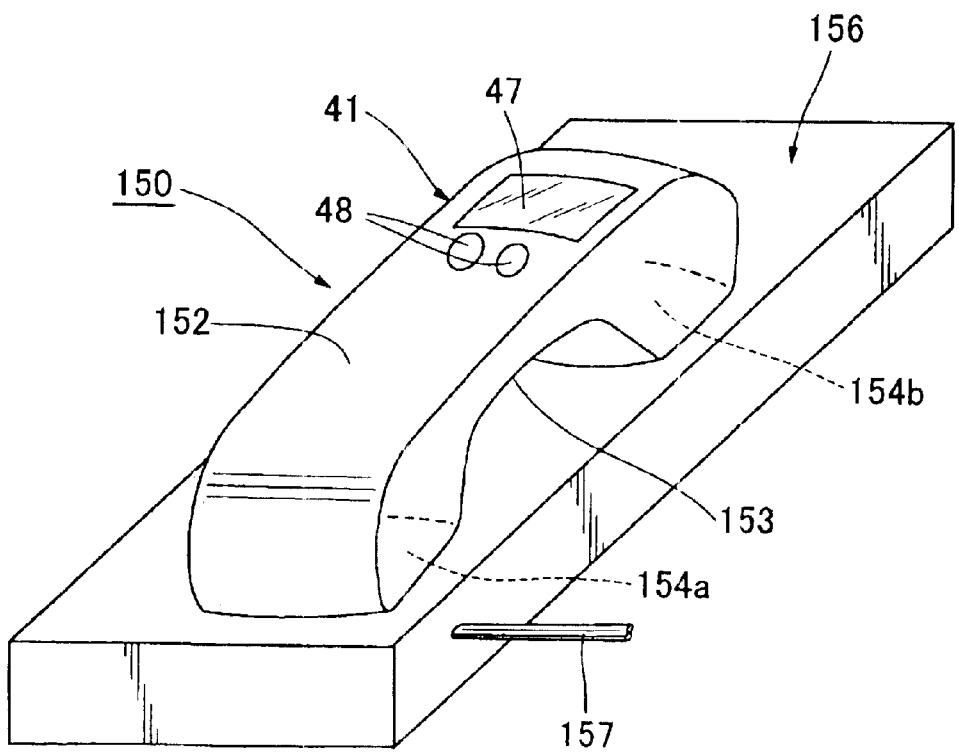
FIG. 20 shows the top side of a bioelectrical impedance measuring apparatus according to the ninth embodiment of the present invention.
Figure 21:
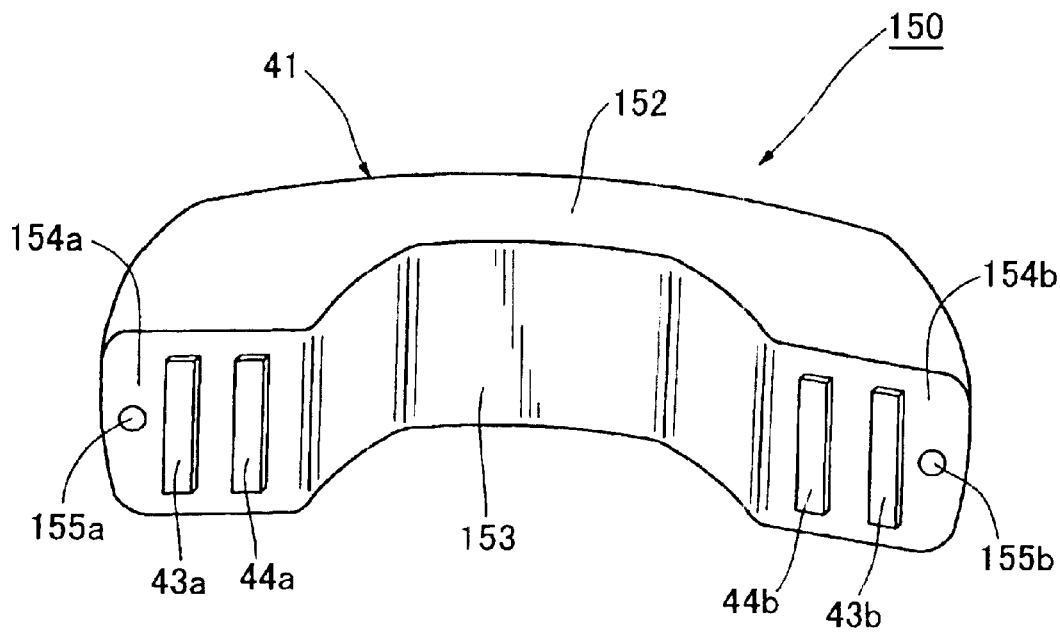
FIG. 21 shows the bottom side of the bioelectrical impedance measuring apparatus of FIG. 20.
Figure 22:
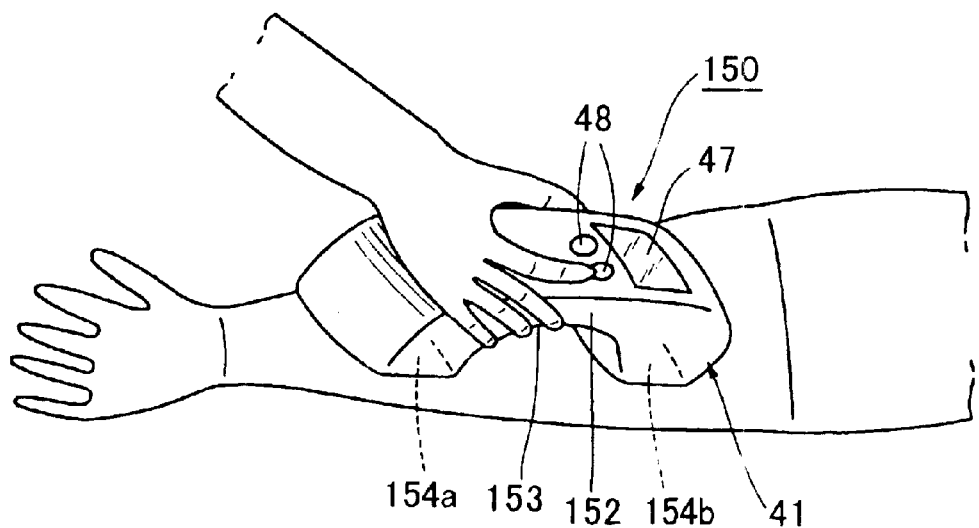
FIG. 22 shows how the bioelectrical impedance is measured with the bioelectrical impedance measuring apparatus of FIG. 20.

FIG. 20 illustrates the external appearance of a bioelectrical impedance measuring apparatus according to the ninth embodiment as viewed from the top side thereof, showing how some parts are arranged on the top side of the housing 41. FIG. 21 illustrates the external appearance of the bioelectrical impedance measuring apparatus of FIG. 20 as viewed from the bottom side thereof, showing how some parts are arranged on the bottom side of the housing 41. FIG. 22 shows how the bioelectrical impedance is measured with the bioelectrical impedance measuring apparatus of FIG. 20. In these drawings, the same parts as those of the first embodiments are identified by the same reference numerals (see FIG. 4).

As shown in FIG. 22, the measuring apparatus 150 is designed to measure the bioelectrical impedance appearing between two selected points on the forearm while applying the measuring apparatus 150 to the forearm by holding it in one hand. The measuring apparatus 150 looks like a handset of standard table telephone, which handset includes a stick-like grip portion having a substantially rectangular shape in section and two projections projecting from both opposite ends of the grip portion in the same direction to form a recess surrounded by the grip portion and the two projections.

As show in the FIGS. 20 to 22, the housing 41 is as large as the palm, permitting the user to hold it in the hand easily. The housing 41 includes two contact surfaces 154a and 154b to be applied on the forearm, and a grip portion 152 to be held in the hand. A charging electrode 155a, a current electrode 43a, a voltage electrode 44a, another voltage electrode 44b, another current electrode 43b, another charging electrode 155b are fixed on the contact surfaces 154a, 154b in the order named to align in the longitudinal direction of the housing 41. Each of the current and voltage electrodes 43a, 43b, 44a, 44b traverses the longitudinal direction of the housing 41. A recess 153 is formed in such a way between the paired voltage electrodes 44a and 44b, or between two contact surfaces 154a and 154b that the measuring apparatus 150 has an arch-like shape. The recess 153 permits the contact surface space to be reduced so that the contact surface exists only near the circumference of the electrodes 155a, 43a, 44a, 44b, 43b, 155b by permitting the electrode-free contact surface space to be eliminated from the contact surface space. Also, the recess 153 permits the grip portion 152 to have a shape facilitating the holding thereof.

On the top side of the housing 41, a display part 47, and input keys 48 are provided. The display part 47 shows some helpful guidance of operation, the progressing of measurement, the results of measurement, the results of arithmetic operation, and such like. The display part 47 of this measuring apparatus 150 is so arranged that the vertical direction of the display part 47 is orthogonally traverse to the longitudinal direction in which the electrodes 155a, 43a, 44a, 44b, 43b, 155b are aligned side by side. Such arrangement of the display part 47 facilitates the seeing of the information appearing on the display part 47 by the user thereof while the measuring apparatus 150 is being held in one hand by the user and applied to the other forearm.

The measuring apparatus 150 may be charged with electricity by laying it on the charger 156 with its charging electrodes 155a, 155b put in contact with the terminals (not shown) of the charger 156. In charging the charger 156 is connected to the outlet via its electric cord 157.

The major parts installed in the housing 41 are similar to those of the first embodiment (see FIG. 5), although a pair of charging terminals 62a, 62b are included in the first section and the power supply terminal 62 is not included in it. The power distributor 61 is charged through a pair of charging electrodes 155a, 155b. It, in responsive to a start or stop command inputted by the depression of the input keys 48, starts or stops electric power supply to each part of the measuring apparatus 150.

In this particular embodiment, the series of actions taken for measuring the bioelectrical impedance are similar to those in the first embodiment (see FIG. 6), except for step 11. At step 11, the user holds the measuring apparatus 150 in one hand and applies the contact surface 154a, 154b to his forearm to put the electrodes 43a, 44a, 44b, 43b in contact with his forearm. The measurement starts when he depresses the input keys 48 with a finger of the hand holding this measuring apparatus 150 to input a command for starting the measurement.

This measuring apparatus 150 is as large as the palm, permitting the user to hold it in one hand easily. The grip portion 152 is so shaped that the user can hold it in one hand easily. These facilitate the holding of the measuring apparatus 150 in one hand by allowing the fingers to insert in the recess 153.

Advantageously the limited contact areas can be closely applied to the muscular forearm because of absence of the contact surface intervening between the voltage electrodes 44a and 44b, which would be interfered with brawny rises, thereby making the contact surfaces 154a and 154b float above the forearm. Also, the electrodes 43a, 43b, 44a, 44b on the contact surface can be applied to the forearm under controlled pressure.

The display part 47 of this measuring apparatus 150 is so arranged that the vertical direction of the display part 47 is orthogonally traverse to the longitudinal direction of the contact surface 154a, 154b. Such arrangement of the display part 47 facilitates the seeing of the information appearing on the display part 47 while the measuring apparatus 150 is being held in one hand by the user thereof and applied to the other forearm.

The measuring apparatus 150 is as large as the palm, permitting the user to hold it with one hand easily, and its grip portion 152 is so shaped that the user can hold it easily. In making a required measurement it suffices that the measuring apparatus 150 be applied to one selected body region such as forearm, which eliminates the inconveniences of handling elongated cables and applying electrodes to the forearm. For these reasons a person who cares for disabled or sick people or children can conveniently use the measuring apparatus to make required measurements for them.

The aforementioned first to ninth embodiments may be modified in various ways as for instance follows.

The first to ninth embodiments are designed to measure the bioelectrical impedance appearing between two points selected on one forearm. Measurement of bioelectrical impedance may be effected on any selected body region such as the part of either leg below the knee and above the ankle. It should be noted that the paired different electrodes be so apart from each other that only one selected body region between joints may be allowed to traverse and contact them, thereby assuring that the part under measurement be put in stationary position.

In the first to ninth embodiments, as referred to above, the extra-cellular water, intra-cellular water and such like can be calculated from the measured bioelectrical impedance. Pulse and blood pressure may be calculated from the measured bioelectrical impedance, also.

The first to eighth embodiments are described as having a semi-cylindrical trough-like forearm rest, which should not be understood as being limitative; flat plate or any other shaped object may be used as long as the one selected body region may be placed to be in close contact with the electrodes.

The measuring apparatus according to the first to sixth embodiments may be so modified that it may be equipped with two opposite extendable sliders having a stick grip or an elbow rest respectively for making the forearm take same position for each measurement more accurately. The stick-like grip may extends horizontal rather than vertical in the first embodiment. Specifically the horizontal grip may cross the longitudinal direction of the trough-like forearm rest. With this arrangement the forearm can be laid on the rear side, allowing the electrodes to be put in contact with the hair-less side of the forearm. This contributes to improvement of accuracy in measurement. The measuring apparatus may be modified to measure the bioelectrical impedance appearing between two points selected on the part of either leg below the knee and above the ankle instead of the forearm by using a heel rest as a positioning member.

The third to sixth embodiments are described as having a semi-cylindrical dome-like cover member, which should not be understood as being limitative; flat plate or any other shaped object may be used as long as the cover member may push the one selected body region against the electrodes well, or specifically in the fifth to sixth embodiments having the electrodes fixed on the cover member, the electrodes may be put in close contact with the forearm.

In the third to sixth embodiments, the cover member is pivotally fixed to the forearm rest with friction large enough to prevent the cover member from rotating or opening easily, a latch member or such like may be provided to prevent the cover member from rotating or opening easily. The length of such latch member may be adjustable, as the size of the body varies with individuals. The cover member may be formed of an elastic material such as a rubber band. One end of the elastic cover member may be permanently fixed to the forearm rest, and the other counter end may be releasably fixed to the forearm rest by a latch member or such like. The press member may be formed of a flexible material such as fabric or cloth. The one end of the flexible cover member may be permanently fixed to the forearm rest, and the other counter end may be releasably fixed to the cover member itself by a hook or such like after lapping the one selected body region under measurement in the flexible cover member.

The seventh to eighth embodiments are described as having a substantially rectangular-planner housing, the housing may be of any other shape such as polygonal prism including triangular prism, trough, and semi-cylinder.

In the seventh to ninth embodiments, the display part is provided on the top surface confronting the contact surface, which should not be understood as being limitative; the display part may be so placed on any selected surface other than the contact surface as long as the user is able to easily see while applying the measuring apparatus to the one selected body region.

The ninth embodiment is described as having the handgrip which is so formed to surround the recess. As a substitute of such handgrip, a knob or a handle which is so shaped to hold it by one hand easily may be provided on the surface confronting the contact surface.

The ninth embodiment is described as having the charging electrodes on the contact surface. Preferably, the charging electrodes may be provided on any selected surface other than the contact surface. Such arrangement of the charging electrodes permits the contact surface area to be reduced and thus, the so reduced contact surface contributes to put the current and voltage electrodes in close contact with one selected body region.

The measuring apparatus of the ninth embodiment is rechargeable, which is preferable in view of operability. Alternatively, the measuring apparatus may be so modified to be dry battery-powered, or to be powered by connecting to the outlet via its electric cord.

Tenth Embodiment

The tenth embodiment relates to a bioelectrical impedance measuring apparatus which measures the bioelectrical impedance of a living body, and relates to a bioelectrical impedance measuring apparatus which measures body fat, body water, pulse, blood pressure and such like as well as bioelectrical impedance of a living body. Particularly, it relates to a hand-held electrode type of bioelectrical impedance measuring apparatus. In use of such type of the measuring apparatus a user raises it by both hands while positioning the palms to substantially confront each other at a predetermined interval.

Figure 1:
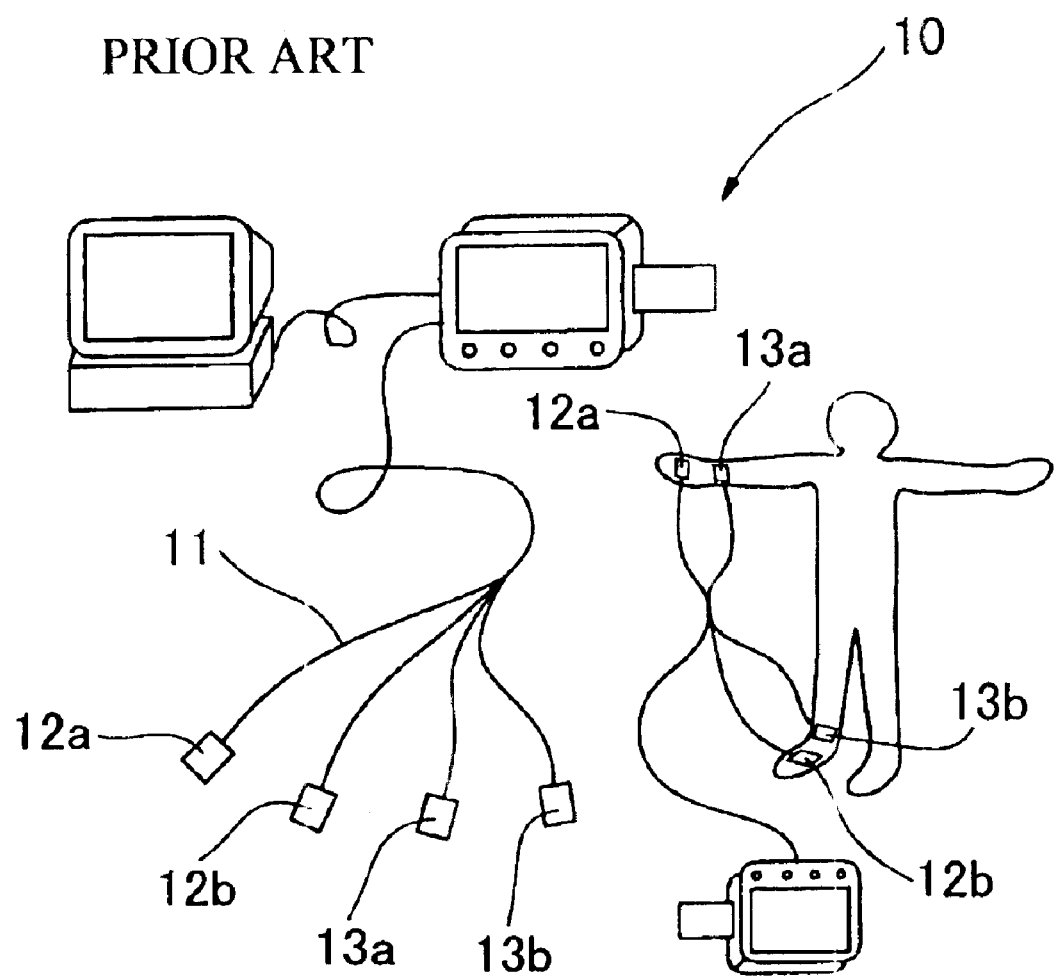
FIG. 1 illustrates a conventional cable-connected electrode type of bioelectrical impedance measuring apparatus.
Figure 2:
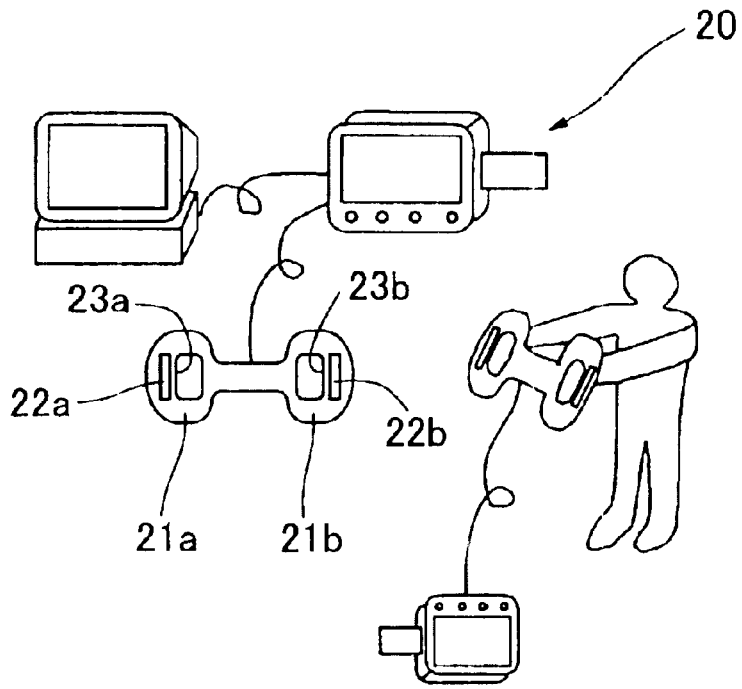
FIG. 2 illustrates a conventional hand-held electrode type of bioelectrical impedance measuring apparatus.
Figure 3:
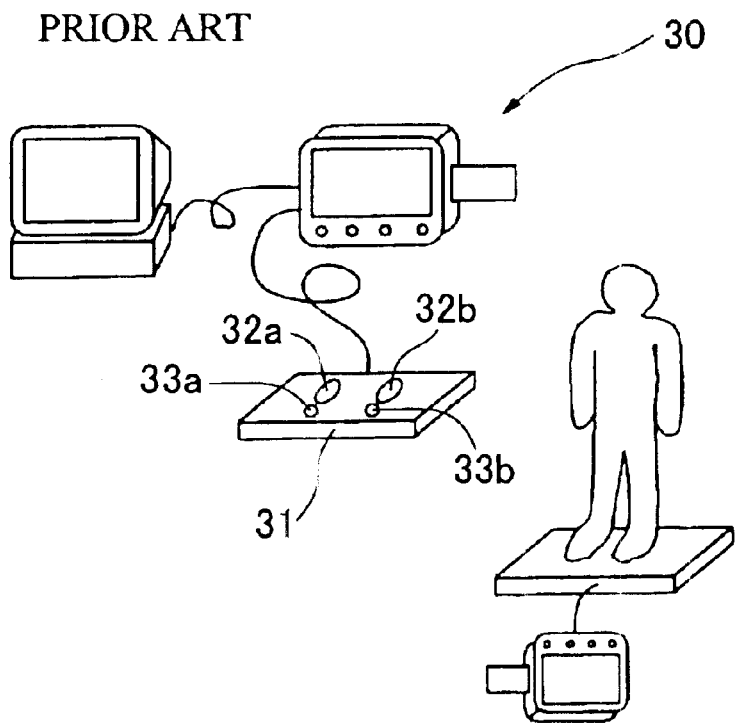
FIG. 3 illustrates a conventional foot sole-contacting electrode type of bioelectrical impedance measuring apparatus.

An example of such type of bioelectrical impedance measuring apparatus is shown in FIG. 2. As shown in the drawing, the measuring electrode apparatus 20 has a pair of current electrodes 22a, 22b and a pair of voltage electrodes 23a, 23b placed on its opposite grips 21a, 21b. In measuring bioelectrical impedance, a user positions both palms to substantially confront each other at a predetermined distance, and holds the paired grips 21a, 21b to put the fingers in contact with the electrodes 22a, 22b, 23a, 23b. Then, he raises the measuring apparatus 20 by both hands while standing up and stretching both arms frontward of the body in approximately horizontal direction.

In this conventional bioelectrical impedance measuring apparatus 20, it is difficult to orient and keep the hands holding the grips in correct position while effecting a required measurement or at every occurrence of measurement.

The measurement is made while putting both hands, particularly fingers, in contact with the electrodes, and thus the total electrode area to be in contact with the hands may be so small that the contact resistance at the electrode area is enlarged, which causes inaccurate measurement.

As the measuring apparatus is held and raised in both hands, particularly fingers while effecting a required measurement, unnecessary force is applied to joints of wrists or arms, which causes inaccurate measurements. In addition, the holding of the measuring apparatus in both hands causes the user to drop the measuring apparatus during measurement.

Thus, it is an object of the bioelectrical impedance measuring apparatus of this embodiment to provide an improved bioelectrical impedance measuring apparatus which is capable of measuring bioelectrical impedance accurately and which is not dropped during measurement.

To attain this object, an improved hand-held electrode type of bioelectrical impedance measuring apparatus is provided. It comprises: a pair of thumb-insert apertures in which both thumbs may be inserted respectively; a pair of thumb electrodes so placed that the thumbs inserted in the apertures may be put in contact with them respectively; a pair of palm electrodes so placed that both palms may be put in contact with them respectively; an alternating current supplying device AC which supplies the paired thumb electrodes; a voltage measuring device which measures the voltage appearing between the pair of palm electrodes; and the arithmetic unit which calculates the bioelectrical impedance according to the supplying alternating current and the measured voltage.

Figure 23:
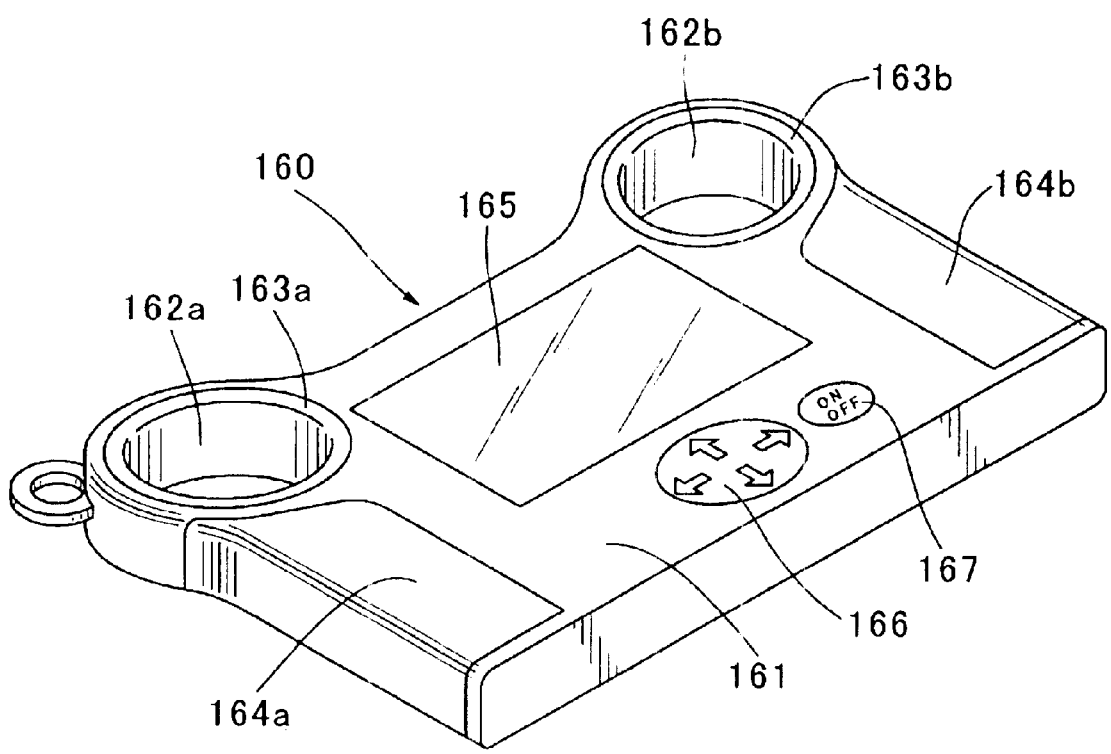
FIG. 23 shows the external appearance of a bioelectrical impedance measuring apparatus according to the tenth embodiment of the present invention.

FIG. 23 shows the external appearance of a bioelectrical impedance measuring apparatus according to the tenth embodiment of the present invention, showing how some parts are arranged on the front face of the housing 161. The measuring apparatus 160 is so shaped and so sized that a user raises it by both hands while positioning the palms to substantially confront each other at a predetermined interval.

The housing 161 is of substantially box shape. On the left side of the housing 161, a left thumb-insert aperture 162a is so formed that it substantially linearly penetrates the housing 161 from left upper portion of the front face of the housing 161 to left upper portion of the rear face of the housing 161. A cylindrical left-thumb electrode 163a is so provided to cover the whole wall of the left-thumb-inset aperture 162a. A left-palm electrode 164a is provided under the left-thumb-insert aperture 162a to cover the left side portion of the housing 161.

Correspondingly, on the right side of the housing 161, a right-thumb-insert aperture 162b is so formed that it substantially linearly penetrates the housing 161 from right upper portion of the front face of the housing 161 to right upper portion of the rear face of the housing 161. A cylindrical right-thumb electrode 163b is so provided to cover the whole wall of the right-thumb-inset aperture 162b. A right-palm electrode 164b is provided under the right-thumb-insert aperture 162b to cover the right side portion of the housing 161.

On the front face of the housing 161, there are provided a display part 165, an operation key 166, and a power "ON/OFF" key 167. The display part 165 shows some helpful guidance of operation, the progressing of measurement, the results of measurement, the results of arithmetic operation, and such like. The operation key 166 enables the user to data such as instructions for controlling the measuring apparatus 160 and user's personal particulars required for measurements. The power "ON/OFF" key 167 enables the user to make the measuring apparatus 160 turn on and off.

The major parts installed in the housing 161 are same as those of the first embodiment (see FIG. 5). In referring to FIG. 5 and the associated description thereof, it should be noted that the left and right-thumb electrodes 163a and 163b correspond the pair of current electrodes 43a, 43b of the first embodiment, and the left and right-palm electrodes 164a and 164b correspond the pair of voltage electrodes 44a, 44b of the first embodiment. The display part 161, the operation key 166 and the power "ON/OFF" key correspond to the display part 47, the input keys 48 and the power "ON" and "OFF" keys 49a, 49b of the first embodiment respectively.

In this particular embodiment, the series of actions taken for measuring the bioelectrical impedance of this embodiment are similar to those of the aforementioned first embodiment (see FIG. 6), except for step 11. At step 11, the user puts the measuring apparatus 160 in front of him to confront the front face of the housing 161, and inputs a command to start the measurement by depressing the operation key 166. The left and right thumbs are inserted in the left and right-thumb-insert apertures 162a and 162b respectively, and the so inserted thumbs are put in contact with the left and right-thumb electrodes 163a and 163b respectively. The left and right palms are put in contact with the left and right-palm electrodes 164a and 164b respectively. When putting both hands on this measuring apparatus 160 in this manner, both palms are consequently positioned to substantially confront each other at a predetermined interval on both sides of this measuring apparatus 160. Keeping this position, this measuring apparatus 160 is raised with holding it from both sides in both hands, particularly palms, and the measurement is made while standing up and stretching both arms frontward of the body in approximately horizontal direction.

The thumbs of both hands are inserted in the thumb-insert apertures 162a, 162b, which has the effect of orienting and keeping both hands in correct position while effecting a required measurement and at every occurrence of measurement.

Both hands, particularly the palms are put in contact with the left and right-palm electrodes 164a and 164b respectively in using the measuring apparatus 160, while particularly fingers are put in contact with the electrodes in using the conventional measuring apparatus. Thus, the total electrode area to be in contact with the hands is enlarged in using the measuring apparatus 160, making the contact resistance at the electrode area smaller.

Thanks to the insertion of both thumbs in the apertures during measurement, even if the user loses his strength of palms, this measuring apparatus may be caught by the thumbs, thus preventing it from dropping.

The thumb electrodes are used as the current electrodes, and the palm electrodes are used as the voltage electrodes. Alternatively, the thumb electrodes may be used as the voltage electrodes, and the palm electrodes may be used as the current electrodes.

The thumb electrodes are so placed to cover the whole wall of the thumb-insert apertures. Alternatively, the thumb electrodes may be so arranged to cover only the bottom part of the walls as long as the inserted thumbs may be put in contact with them.

The measuring apparatus 160 is powered from the external power source by connecting it to the outlet via its electric cord for example. Alternatively, it may be rechargeable or dry battery-powered.

The extra-cellular water, intra-cellular water and such like can be calculated from the measured bioelectrical impedance. Pulse and blood pressure may be calculated from the measured bioelectrical impedance, also.

What is claimed is:

1. A bioelectrical impedance measuring apparatus characterized in that it comprises:
    a housing having a contact surface to be applied to one selected body region, the housing having a first pair of current electrodes, a first pair of voltage electrodes, an alternative current supplying device, a voltage measuring device and an arithmetic unit equipped therewith;
    the first pair of current electrodes so placed on the contact surface that the one selected body region may be put in contact with the current electrodes; and
    the first pair of voltage electrodes so placed on the contact surface between the pair of current electrodes that the selected one body region may be put in contact with the voltage electrodes;
    the alternating current supplying device supplying the first pair of current electrodes with alternating current;
    the voltage measuring device measuring the voltage appearing between the pair of voltage electrodes; and
    the arithmetic unit calculating the bioelectrical impedance from the supplying alternating current and the measured voltage;
    wherein the first pair of current electrodes and the first pair of voltage electrodes stand in one line.

2. A bioelectrical impedance measuring apparatus according to claim 1 wherein the housing includes a rest whose upper surface defines the contact surface to be applied to the selected one body region, the contact surface being like a semi-cylindrical trough, and the current and voltage electrodes being so curved that they may be almost coplanar with the semi-cylindrical contact surface.

3. A bioelectrical impedance measuring apparatus according to any of claim 2 wherein it further comprises a positioning member which permits the one selected body region to be put in correct position, the positioning member being capable of effecting so positional adjustment as to fit on the one selected body region.

4. A bioelectrical impedance measuring apparatus according to claim 3 wherein the one selected body region is the right or left forearm, and the positioning member is a hand grip and/or an elbow rest.

5. A bioelectrical impedance measuring apparatus according to claim 1 wherein it further comprises a cover member capable of pushing the one selected body region against the two pairs of electrodes.

6. A bioelectrical impedance measuring apparatus according to claim 5 wherein:
    a second pair of current electrodes and a second pair of voltage electrodes are placed on the surface of the cover member which surface confronts the contact surface of the rest, the second electrodes being arranged in the same order and at same intervals as the counter first electrodes, thus sandwiching the one selected body region therebetween;
    the alternating current supplying device supplies one and same alternating current to the first and second pairs of current electrodes simultaneously, making the two sets of confronting current electrodes function as a single composite pair of current electrodes; and
    the voltage measuring device measures the voltage appearing between the first and second pairs of voltage electrodes, making the two sets of confronting voltage electrodes function as a single composite pair of voltage electrodes.

7. A bioelectrical impedance measuring apparatus according to claim 1 wherein the housing includes a rest whose upper surface defines the contact surface to be applied to the one selected body region, and a cover member pivotally fixed to one longitudinal edge of the rest, thereby permitting the one selected body region to be sandwiched between the rest and the cover member which is put in its closed position; and
    the first pairs of current and voltage electrodes are placed on the surface of the cover member instead of the contact surface to push the two pairs of electrodes against the one selected body region lying on the contact surface of the rest.

8. A bioelectrical impedance measuring apparatus according to claim 7 wherein it further comprises a positioning member which permits the one selected body region to be put in correct position, the positioning member being capable of effecting so positional adjustment as to fit on the one selected body region.

9. A bioelectrical impedance measuring apparatus according to claim 8 wherein the one selected body region is the right or left forearm, and the positioning member is a hand grip and/or an elbow rest.

10. A bioelectrical impedance measuring apparatus according to claim 1 wherein the one selected body region is the right or left forearm.

11. A bioelectrical impedance measuring apparatus according to claim 1 wherein the one selected body region is the part of the right or left leg below the knee and above the ankle.

12. A bioelectrical impedance measuring apparatus according to claim 1 wherein it further comprises a display placed on a selected place of the housing other than the contact surface.

13. A bioelectrical impedance measuring apparatus according to claim 12 wherein the housing is so shaped and sized that a user can hold it in one hand while applying the contact surface to the one selected body region, still permitting the display to remain in sight.

14. A bioelectrical impedance measuring apparatus according to claim 13 wherein the housing has indentations formed on its opposite sides, on which indentations the fingers are placed, thereby facilitating the holding of the housing in one hand.

15. A bioelectrical impedance measuring apparatus according to any one of claim 12 wherein the display is so arranged that the vertical direction of the display is orthogonally traverse to the direction in which the first pairs of current and voltage electrodes are aligned side by side, thereby facilitating the seeing of the information appearing in its screen.

16. A bioelectrical impedance measuring apparatus according to claim 1 wherein:
    the housing has a display placed at a selected place other than the contact surface and a grip portion;

a recess is so formed between the first pair of voltage electrodes that the contact surface space is reduced.

17. A bioelectrical impedance measuring apparatus according to claim 16 wherein the housing is so shaped and sized that a user can hold it with one hand while applying the contact surface to the one selected body region, still permitting the display to remain in sight.

18. A bioelectrical impedance measuring apparatus according to claim 16 wherein the grip portion is so formed to surround the recess, thereby facilitating the holding of the housing in one hand.

19. A bioelectrical impedance measuring apparatus according to any one of claim 16 wherein the display is so arranged that the vertical direction of the display is orthogonally traverse to the direction in which the first pairs of current and voltage electrodes are aligned side by side, thereby facilitating the seeing of the information appearing in its screen.

20. A bioelectrical impedance measuring apparatus according to claim 1 wherein the arithmetic unit further calculates at least one of body fat, body water, pulse, or blood pressure.

21. A bioelectrical impedance measuring apparatus according to claim 1 wherein:
   the alternating current supplying device supplies a plurality of alternating currents of different frequencies;
   the voltage measuring device measures the voltage every time when an alternating current of selected frequency is supplied; and
   the arithmetic unit calculates the bioelectrical impedance values from each alternating current and corresponding voltage.

22. A bioelectrical impedance measuring apparatus according to claim 21 wherein the arithmetic unit further calculates at least one of the ratio between extra-cellular water and intra-cellular water, the ratio of body water and extra-cellular water, intra-cellular water, extra-cellular water, body water, or body fat.

23. A bioelectrical impedance measuring apparatus according to claim 1 wherein:
   the alternating current supplying device supplies an alternating current of a single frequency;
   the voltage measuring device further measures the phase of the voltage measured by it; and
   the arithmetic unit further calculates the phase difference between the phase of the supplying alternating current and the phase of the measured voltage.

24. A bioelectrical impedance measuring apparatus characterized in that it comprises:
   a rest on which one selected body region may be put;
   a pair of current electrodes so placed on the rest that the one selected body region may be put in contact with the current electrodes;
   a pair of voltage electrodes so placed on the contact surface between the pair of current electrodes that the one selected body region may be put in contact with the voltage electrodes;
   a position member which permits the one selected body region to be put in correct position;
   an alternating current supplying device which supplies the pair of current electrodes with alternating current;
   a voltage measuring device which measures the voltage appearing between the pair of voltage electrodes; and
   an arithmetic unit which calculates the bioelectrical impedance from the supplying alternating current and the measured voltage.

25. A bioelectrical impedance measuring apparatus characterized in that it comprises;
   a rest on which one selected body region may be put;
   a pair of current electrodes so placed on the rest that the one selected body region may be put in contact with the current electrodes;
   a pair of voltage electrodes so placed on the contact surface between the pair of current electrodes that the one selected body region may be put in contact with the voltage electrodes;
   a cover member capable of pushing the one selected body region against the two pairs of electrodes;
   an alternating current supplying device which supplies the pair of current electrodes with alternating current;
   a voltage measuring device which measures the voltage appearing between the pair of voltage electrodes; and
   an arithmetic unit which calculates the bioelectrical impedance from the supplying alternating current and the measured voltage.

26. A bioelectrical impedance measuring apparatus characterized in that it comprises:
   a rest on which one selected body region may be put;
   a cover member so pivotally fixed to one longitudinal edge of the rest that the one selected body region may be sandwiched between the rest and the cover member which is put in its closed position;
   a pair of current electrodes and a pair of voltage electrodes so placed on the surface of the cover member to push the two pairs of electrodes against the one selected body region lying on the contact surface of the rest, the pair of voltage electrodes intervening between the pair of current electrodes;
   an alternating current supplying device which supplies the pair of current electrodes with alternating current;
   a voltage measuring device which measures the voltage appearing between the pair of voltage electrodes; and
   an arithmetic unit which calculates the bioelectrical impedance from the supplying alternating current and the measured voltage.

27. A bioelectrical impedance measuring apparatus characterized in that it comprises:
   a housing having a contact surface to be applied to one selected body region and a grip portion, the housing having an alternating current supplying device, a voltage measuring device and an arithmetic unit equipped therewith;
   a pair of current electrodes so placed on the contact surface that the one selected body region may be put in contact with the current electrodes;
   a pair of voltage electrodes so placed on the contact surface between the pair of current electrodes that the selected one body region may be put in contact with the voltage electrodes; and
   a display placed on a selected place of the housing other than the contact surface;
   the alternating current supplying device supplying the first pair of current electrodes with alternating current;
   the voltage measuring device measuring the voltage appearing between the pair of voltage electrodes;
   the arithmetic unit calculating the bioelectrical impedance from the supplying alternating current and the measured voltage; and
   a recess being so formed between the first pair of voltage electrodes that the contact surface space is reduced.

* * * * *